United States Patent
Heltzel et al.

(10) Patent No.: US 12,194,448 B2
(45) Date of Patent: Jan. 14, 2025

(54) CATALYSTS FOR THE TRANSFORMATION OF CARBON DIOXIDE AND GLYCEROL TO FORMIC ACID AND LACTIC ACID AND METHODS OF MAKING THE SAME

(71) Applicant: The George Washington University, Washington, DC (US)

(72) Inventors: Jacob Mark Heltzel, Washington, DC (US); Matthew Thomas Finn, Chevy Chase, MD (US); Adelina Mitkova Voutchkova, Silver Spring, MD (US); Arturo Azua, Arlington, VA (US)

(73) Assignee: The George Washington University, Washington, DC (US)

(*) Notice: Subject to any disclaimer, the term of this patent is extended or adjusted under 35 U.S.C. 154(b) by 31 days.

(21) Appl. No.: 16/614,713

(22) PCT Filed: May 21, 2018

(86) PCT No.: PCT/US2018/033624
§ 371 (c)(1),
(2) Date: Nov. 18, 2019

(87) PCT Pub. No.: WO2018/213821
PCT Pub. Date: Nov. 22, 2018

(65) Prior Publication Data
US 2020/0171474 A1    Jun. 4, 2020

Related U.S. Application Data

(60) Provisional application No. 62/508,509, filed on May 19, 2017.

(51) Int. Cl.
B01J 31/00      (2006.01)
B01J 31/16      (2006.01)
(Continued)

(52) U.S. Cl.
CPC ......... B01J 31/1616 (2013.01); B01J 31/181 (2013.01); B01J 31/223 (2013.01);
(Continued)

(58) Field of Classification Search
None
See application file for complete search history.

(56) References Cited

U.S. PATENT DOCUMENTS

2009/0299009 A1* 12/2009 Yonehara ................ B01J 23/44
                                                                    525/55
2010/0130763 A1*  5/2010 Gao ........................ C07C 67/03
                                                                    554/124
(Continued)

FOREIGN PATENT DOCUMENTS

CN         106140299 A   * 11/2016
WO    WO-2014/056005 A1    4/2014

OTHER PUBLICATIONS

Azua et al. (ACS Sustainable Chemistry & Engineering, 5, 3963-3972, published on Mar. 27, 2017). (Year: 2017).*
(Continued)

Primary Examiner — Yun Qian
(74) Attorney, Agent, or Firm — BLANK ROME LLP

(57) ABSTRACT

Catalysts and methods for transformation of glycerol and a carbon feedstock, such as $CO_2$, a carbonate salt or a bicarbonate salt, are described herein. Homogeneous catalysts include compounds of formula M[NHC-R-linker]aLbXc, where M is a transition metal, NHC is an N-heterocyclic carbene ligand, R is an alkyl or aryl group, linker is a polar group, L is a neutral ligand, X is an anionic ligand, a ranges from 1-3, b ranges from 0-3, and c ranges from 0-3. Heterogeneous catalysts include a solid support with a catalytically active compound immobilized on the solid support, where the catalytically active compound has the formula M[NHC-R-linker]aLbXc where M is a transition
(Continued)

metal, NHC is an N-heterocyclic carbene ligand, R is an alkyl or aryl group; linker is a polar group, L is a neutral ligand, X is an anionic ligand, a ranges from 1-3, b ranges from 0-3, and c ranges from 0-3.

20 Claims, 15 Drawing Sheets

(51) Int. Cl.
  B01J 31/18   (2006.01)
  B01J 31/22   (2006.01)
  C07C 51/15   (2006.01)

(52) U.S. Cl.
  CPC ......... *C07C 51/15* (2013.01); *B01J 2231/625* (2013.01); *B01J 2531/0244* (2013.01); *B01J 2531/821* (2013.01); *B01J 2531/822* (2013.01); *B01J 2531/827* (2013.01); *B01J 2531/845* (2013.01); *C07C 2531/12* (2013.01)

(56) References Cited

U.S. PATENT DOCUMENTS

| | | | |
|---|---|---|---|
| 2011/0160412 A1* | 6/2011 | Thieuleux | B01J 31/0295 526/126 |
| 2012/0253067 A1 | 10/2012 | Chaudhari et al. | |

OTHER PUBLICATIONS

Kuhn et al. Organometallics, 32, 741-744 (Year: 2013).*
Peris et al. (Organometallics, 2010, 29, 3661-3664). (Year: 2010).*
CN 106140299 A, Machine-generated English translation is attached (Year: 2016).*
Azua et al. (ACS Sustainable Chemistry & Engineering, 2017, 5, 3963-3972 (Year: 2017).*
International Search Report and Written Opinion for PCT/US2018/033624, dated Aug. 23, 2018, 8 pages.
N. Galy, et al., "Glycerol in Subcritical and Supercritical Solvents", Journal of Chemical Technology; Biotechnology; vol. 92; Issue 1; 1 page.
Z. Sun, et al., "Robust Iridium Coordination Polymers: Highly Selective, Efficient, and Recyclable Catalysts for Oxidative Conversion of Glycerol to Potassium Lactate with Dihydrogen Liberation", ACS Publications, vol. 5, No. 11, 2015, 25 pages.
M. Aresta, et al., "Catalysis for the Valorization of Exhaust Carbon: from $CO_2$ to Chemicals, Materials, and Fuels. Technological Use of $CO_2$,", Chemical Reviews, 2014, 114, pp. 1709-1742.
D. Jantke, et al., "Hydrogen Production and Storage on a Formic Acid/Bicarbonate Platform using Water-Soluble N-Heterocyclic Carbene Complexes of Late Transition Metals", ChemSusChem, 2016, No. 9. pp. 2849-2854.
A. Dibenedetto, et al., "$Ru^{11}$-Mediated Hydrogen Transfer from Aqueous Glycerol to $CO_2$: From Waste to Value-Added Products", ChemSusChem, 2011, No. 4, pp. 1311-1315.
Albert, et al., Formic Acid-Based Fischer?Tropsch Synthesis for Green Fuel Production from Wet Waste Biomass and Renewable Excess Energy, ACS Sustainable Chem. Eng., 2016, 4:5078-5086.
Albrecht, et al., Chelated Iridium(III) Bis-carbene Complexes as Air-Stable Catalysts for Transfer Hydrogenation, Organometallics 2002, 21:3596-3604.
Areta, The Versatility of Carbon Dioxide, ChemSusChem, 2010, 3:631-632.
Aridoss, et al., Building Heterocyclic Systems with RC(OR)2+ Carbocations in Recyclable Brønsted Acidic Ionic Liquids: Facile Synthesis of 1-Substituted 1H-1,2,3,4-Tetrazoles, Benzazoles and Other Ring Systems with CH(OEt)3 and EtC(OEt)3 in [EtNH3][NO3] and [PMIM(SO3H) ][OTf], Eur. J. Org. Chem., 2011, 2827-2835.

Artz, et al., Sustainable Conversion of Carbon Dioxide: An Integrated Review of Catalysis and Life Cycle Assessment, Chem. Rev., 2018, 118:434-504.
Azua, et al., Iridium NHC Based Catalysts for Transfer Hydrogenation Processes Using Glycerol as Solvent and Hydrogen Donor, Organometallics, 2011, 30:5532-5536.
Azua, et al., Sulfonate-Functionalized NHC-Based Ruthenium Catalysts for the Isomerization of Allylic Alcohols in Water. Recyclability Studies, Organometallics 2010, 29:3661-3664.
Azua, et al., Transfer Hydrogenation from Glycerol: Activity and Recyclability of Iridium and Ruthenium Sulfonate-Functionalized N?Heterocyclic Carbene Catalysts, ACS Sustainable Chem. Eng., 2017, 5:3963-3972.
Azua, et al., Water-Soluble IrIII N-Heterocyclic Carbene Based Catalysts for the Reduction of CO2 to Formate by Transfer Hydrogenation and the Deuteration of Aryl Amines in Water, Chem. Eur. J., 2011, 17:3963-3967.
Badiei, et al., Cp*Co(III) Catalysts with Proton-Responsive Ligands for Carbon Dioxide Hydrogenation in Aqueous Media, Inorg. Chem., 2013, 52:12576-12586.
Boddien, et al., Efficient Dehydrogenation of Formic Acid Using an Iron Catalyst, Science, 2011, 333:1733-1736.
Bosquain, et al., Aqueous phase carbon dioxide and bicarbonate hydrogenation catalyzed by cyclopentadienyl ruthenium complexes, Appl. Organom et al. Chem., 2007, 21:947-951.
Centi, et al., Catalysis for CO2 conversion: a key technology for rapid introduction of renewable energy in the value chain of chemical industries, Energy Environ. Sci., 2013, 6:1711-1731.
Compound Summary Potassium Formate, 2020, 28 pages.
Crotti, et al., Alternative intermediates for glycerol valorization: iridium-catalyzed formation of acetals and ketals†, Green Chem., 2010, 12:2225-2231.
Diaz-Alvarez, et al., Glycerol and derived solvents: new sustainable reaction media for organic synthesis, Chem. Commun., 2011, 47:6208-6227.
Dibenedetto, et al., Rull-Mediated Hydrogen Transfer from Aqueous Glycerol to CO2: From Waste to Value-Added Products, ChemSusChem, 2011, 4:1311-1315.
Erlandsson, et al., (Pentamethylcyclopentadienyl)iridium-PTA (PTA = 1,3,5-Triaza-7-phosphaadamantane) Complexes and Their Application in Catalytic Water Phase Carbon Dioxide Hydrogenation, Eur. J. Inorg. Chem., 2008, 620-627.
Fang, et al., Huge critical current density and tailored superconducting anisotropy in SmFeAsO0.8F0.15 by low-density columnar-defect incorporation, Nature Communications, 2013, 6 pages.
Federsel, et al., AWell-Defined Iron Catalyst for the Reduction of Bicarbonates and Carbon Dioxide to Formates, Alkyl Formates, and Formamides **, Angew. Chem. Int. Ed., 2010, 49:9777-9780.
Filonenko, et al., The impact of Metal-Ligand Cooperation in Hydrogenation of Carbon Dioxide Catalyzed by Ruthenium PNP Pincer, ACS Catal. 2013, 3:2522-2526.
Finn, et al., Next-Generation Water-Soluble Homogeneous Catalysts for Conversion of Glycerol to Lactic Acid, Organometallics, 2018, 37:1400-1409.
Godoy, et al., Palladium Catalysts with Sulfonate-Functionalized-NHC Ligands for Suzuki-Miyaura Cross-Coupling Reactions in Water, Organometallics 2011, 30:684-688.
Gu, et al., Glycerol as a sustainable solvent for green chemistry, Green Chem., 2010, 12:1127-1138.
Hayashi, et al., Aqueous hydrogenation of carbon dioxide catalysed by water-soluble ruthenium aqua complexes under acidic conditions, Chem. Commun., 2004, 2714-2715.
Himeda, et al., Simultaneous Tuning of Activity and Water Solubility of Complex Catalysts by Acid-Base Equilibrium of Ligands for Conversion of Carbon Dioxide, Organometallics, 2007, 26:3:7:702-712.
Huff, et al., Catalytic CO2 Hydrogenation to Formate by a Ruthenium Pincer Complex, ACS Catal. 2013, 3:2412-2416.
Hull, et al., Reversible hydrogen storage using CO2 and a proton-switchable iridium catalyst in aqueous media under mild temperatures and pressures, Nature Chemistry, 2012, 4:383-388.

(56) References Cited

OTHER PUBLICATIONS

Jantke, et al., Hydrogen Production and Storage on a Formic Acid/Bicarbonate Platform using Water-Soluble N-Heterocyclic Carbene Complexes of Late Transition Metals, ChemSusChem, 2016, 9:2849-2854.
Jantke, et al., Synthesis and Characterization of Highly Water Soluble Ruthenium(II) and Osmium(II) Complexes Bearing Chelating Sulfonated N?Heterocyclic Carbene Ligands, Organometallics, 2013, 32:741-744.
Jessop, et al., Homogeneous Hydrogenation of Carbon Dioxide, Chemical Reviews, 1995, 95:2:259-272.
Jime?nez, et al., Mechanistic Insights into Transfer Hydrogenation Catalysis by [Ir(cod)(NHC)2]+ Complexes with Functionalized N?Heterocyclic Carbene Ligands, Organometallics, 2015, 34:926-940.
Jin, et al., High-yield reduction of carbon dioxide into formic acid by zero-valent metal/metal oxide redox cyclest, Energy Environ. Sci., 2011, 4:881-884.
Joó, et al., Homogeneous hydrogenation of aqueous hydrogen carbonate to formate under mild conditions with water soluble rhodium(I)- and ruthenium(II)-phosphine catalysts, Appl. Organom et al. Chem., 2000, 14:857-859.
Joó, et al., Homogeneous hydrogenation of aqueous hydrogen carbonate to formate under exceedingly mild conditions-a novel possibility of carbon dioxide activationt, Chem. Commun., 1999, 971-972.
Laurenczy, et al., Formation and Characterization of Water-Soluble Hydrido-Ruthenium(II) Complexes of 1,3,5-Triaza-7-phosphaadamantane and Their Catalytic Activity in Hydrogenation of CO2 and HCO3—in Aqueous Solution, Inorg. Chem., 2000, 39:5083-5088.
Leitner, et al., Activation of Carbon Dioxide, IV *. Rhodium-catalysed Hydrogenation of Carbon Dioxide to Formic Acid **, Journal of Organometallic Chembtry, 1994, 475:257-266.
Li, et al., Ruthenium-catalyzed hydrogen generation from glycerol and selective synthesis of lactic acid†, Green Chem., 2015, 17:193-198.
Lu, et al., A Prolific Catalyst for Selective Conversion of Neat Glycerol to Lactic Acid, ACS Catal., 2016, 6:2014-2017.
Lu, et al., Base-free hydrogenation of CO2 to formic acid in water with an iridium complex bearing a N,N'-diimine ligand†, Green Chem., 2016, 18:4553-4558.
Moret, et al., Direct synthesis of formic acid from carbon dioxide by hydrogenation in acidic media, Nature Communications, 2014, 7 pages.
Munshi, et al., Hydrogenation of Carbon Dioxide Catalyzed by Ruthenium Trimethylphosphine Complexes: The Accelerating Effect of Certain Alcohols and Amines, J. Am. Chem. Soc., 2002, 124:7963-7971.
Mura, et al., Formic Acid: A Promising Bio-Renewable Feedstock for Fine Chemicals, Adv. Synth. Catal., 2012, 354:3180-3186.
Ogo, et al., Mechanistic investigation of CO2 hydrogenation by Ru(II) and Ir(III) aqua complexes under acidic conditions: two catalytic systems differing in the nature of the rate determining stept, Dalton Trans., 2006, 4657-4663.

Ohnishi, et al., Ruthenium(II)-Catalyzed Hydrogenation of Carbon Dioxide to Formic Acid. Theoretical Study of Real Catalyst, Ligand Effects, and Solvation Effects, J. Am. Chem. Soc., 2005, 127:4021-4032.
Onishi, et al., CO2 Hydrogenation Catalyzed by Iridium Complexes with a Proton-Responsive Ligand, Inorg. Chem., 2015, 54:5114-5123.
Otto, et al., Closing the loop: captured CO2 as a feedstock in the chemical industry, Energy Environ. Sci., 2015, 8:3283-3297.
Pagliaro, et al., From Glycerol to Value-Added Products, Angew. Chem. Int. Ed. 2007, 46:4434-4440.
Rentzsch, et al., Iridium complexes of N-heterocyclic carbenes in C—H borylation using energy efficient microwave technology: influence of structure, ligand donor strength and counter ion on catalytic activity†, Green Chem., 2009, 11:1610-1617.
Rohmann, et al., Hydrogenation of CO2 to Formic Acid withaHighly Active Ruthenium Acriphos Complex in DMSO and DMSO/Water, Angew. Chem. Int. Ed., 2016, 55:8966-8969.
Sanz, et al., '(n6-arene)Ru(bis-NHC)' complexes for the reduction of CO2 to formate with hydrogen and by transfer hydrogenation with iPrOH, Dalton Trans., 2010, 39:6339-6343.
Sanz, et al., A New Approach to the Reducation of Carbon Dioxide: CO2 Reduction to Formate by Transfer Hydrogenation in iPrOH, Organometallics, 2010, 29:275-277.
Schmeier, et al., Secondary Coordination Sphere Interactions Facilitate the Insertion Step in an Iridium(III) CO2 Reduction Catalyst, J. Am. Chem. Soc. 2011, 133:9274-9277.
Sharma, et al., 2?Propanol vs Glycerol as Hydrogen Source in Catalytic Activation of Transfer Hydrogenation with (?6? Benzene)ruthenium(II) Complexes of Unsymmetrical Bidentate Chalcogen Ligands, Organometallics 2014, 33:3629-3639.
Sharninghausen, et al., Efficient selective and atom economic catalytic conversion of glycerol to lactic acid, Nature Communications, 2014, 9 pages.
Sharninghausen, et al., Selective conversion of glycerol to lactic acid with iron pincer precatalysts†, Chem. Commun., 2015, 51:16201-16204.
Shen, et al., The alcohol-mediated reduction of CO2 and NaHCO3 into formate: a hydrogen transfer reduction of NaHCO3 with glycerine under alkaline hydrothermal conditions, RSC Adv., 2012, 2:797-801.
Sordakis, et al., Homogeneous Catalysis for Sustainable Hydrogen Storage in Formic Acid and Alcohols, Chem. Rev., 2018, 118:372-433.
Su, et al., Simultaneously Converting Carbonate/Bicarbonate and Biomass to Value-added Carboxylic Acid Salts by Aqueous-phase Hydrogen Transfer, ACS Sustainable Chem. Eng., 2015, 3:195-203.
Tanaka, et al., Catalytic Hydrogenation of Carbon Dioxide Using Ir(III)-Pincer Complexes, J. Am. Chem. Soc., 2009, 131:14168-14169.
Weilhard, et al., Selective CO2 Hydrogenation to Formic Acid with Multifunctional Ionic Liquids, ACS Catal. 2018, 8:1628-1634.
West, et al., In Situ Formation of Alkylcarbonic Acids with CO2, J. Phys. Chem. A, 2001, 105:3947-3948.
Zhang, et al., Iron catalyzed CO2 hydrogenation to formate enhanced by Lewis acid co-catalysts†, Chem. Sci., 2015, 6:4291-4299.

* cited by examiner

CATALYSTS FOR THE TRANSFORMATION OF CARBON DIOXIDE AND GLYCEROL TO FORMIC ACID AND LACTIC ACID AND METHODS OF MAKING THE SAME

CROSS-REFERENCE TO RELATED APPLICATION

This application is a national stage of International Patent Application No. PCT/US2018/033624, filed May 21, 2018, which claims the benefit of U.S. Provisional Application No. 62/508,509, filed May 19, 2017, the contents of which are incorporated by reference herein in their entireties.

STATEMENT REGARDING FEDERALLY SPONSORED RESEARCH OR DEVELOPMENT

This invention was made with Government support under Grant/Contract No. CHE-1554963 awarded by the National Science Foundation (NSF). The U.S. government may have certain rights in this invention.

FIELD OF THE INVENTION

The present invention relates to catalysts for the transformation of carbon dioxide ($CO_2$) or carbonate salts and glycerol to formic acid and lactic acid. More specifically, the present invention includes water soluble iridium (Ir) and ruthenium (Ru) N-heterocyclic carbene complexes, as homogeneous catalysts, or Ir and Ru N-heterocyclic carbene complexes immobilized onto a surface of a solid substrate, as heterogeneous catalysts, for the transformation of $CO_2$ or carbonate salts and glycerol to formic acid and lactic acid.

BACKGROUND OF THE DISCLOSURE

Technologies that reduce $CO_2$ have received widespread attention in recent years, further encouraged by government and environmental policy aimed at addressing climate and renewable energy challenges. The low cost and non-hazardous nature of $CO_2$ make it a suitable C1 feedstock for commodity chemicals, including formaldehyde, formic acid (FA) and methanol. FA has found widespread utility as a chemical feedstock, commodity chemical for food and agriculture, as a fuel and a hydrogen storage medium. The most explored method for converting $CO_2$ to FA is direct hydrogenation, where $CO_2$ is reacted with hydrogen gas under high pressures. Catalytic methods for $CO_2$ direct hydrogenation, pioneered in the 1970's, continue to be intensively studied. Homogeneous catalysts with Rh, Ru, Ir, Fe and Co have been reported, with the most efficient systems affording turnover numbers (TONs) in the order of $10^6$. A salient challenge for direct hydrogenation is overcoming the thermodynamic equilibrium of this reversible reaction, which necessitates use of base or amines to stabilize the product as formate salts or adducts. Solvent stabilization via hydrogen bonding in aqueous media has also been shown to drive the equilibrium towards products.

Since $CO_2$ is in pH-dependent equilibrium with $HCO_3^-$ in aqueous media ($pK_{a1}$=6.35 at 25° C.), hydrogenation of bicarbonate has also been demonstrated with Rh, Ru, Ir and Fe. However, reported activities for bicarbonate are often lower than those for $CO_2$, despite the fact that the thermodynamics of bicarbonate hydrogenation in water are reported to be slightly more favorable than that of $CO_2$ ($\Delta G°_{298\,K}$=-2.3 kcal/mol for bicarbonate vs. -1.9 kcal/mol for $CO_2$).

Despite being the most abundant element, hydrogen does not exist on earth in significant amounts as a gas ($H_2$). To provide hydrogen gas in amounts sufficient to make any process industrially viable, hydrogen gas has to formed from hydrogen-containing compounds, such as liquid hydrocarbons or natural gas, that usually display rather high hydrogen-element binding energies. Such processes require high temperatures and thus have large energy demands. Furthermore, copious amounts of $CO_2$ are produced during such processes as a by-product. Additionally, the transfer and use of hydrogen gas is associated with physical hazards, such as flammability. Although a number of highly active catalysts for direct hydrogenation of $CO_2$ have been reported, there is a need for a cheap, abundant and renewable source of hydrogen, rather than pure hydrogen gas.

BRIEF DESCRIPTION OF THE DRAWINGS

FIG. 8 is a contour plot illustrating turnover numbers (TONs) in 24 h for formic acid formation using Catalyst 1a;

FIG. 9 is a contour plot illustrating TONs in 24 h for lactic acid formation using Catalyst 1a;

DETAILED DESCRIPTION

Figure 1:
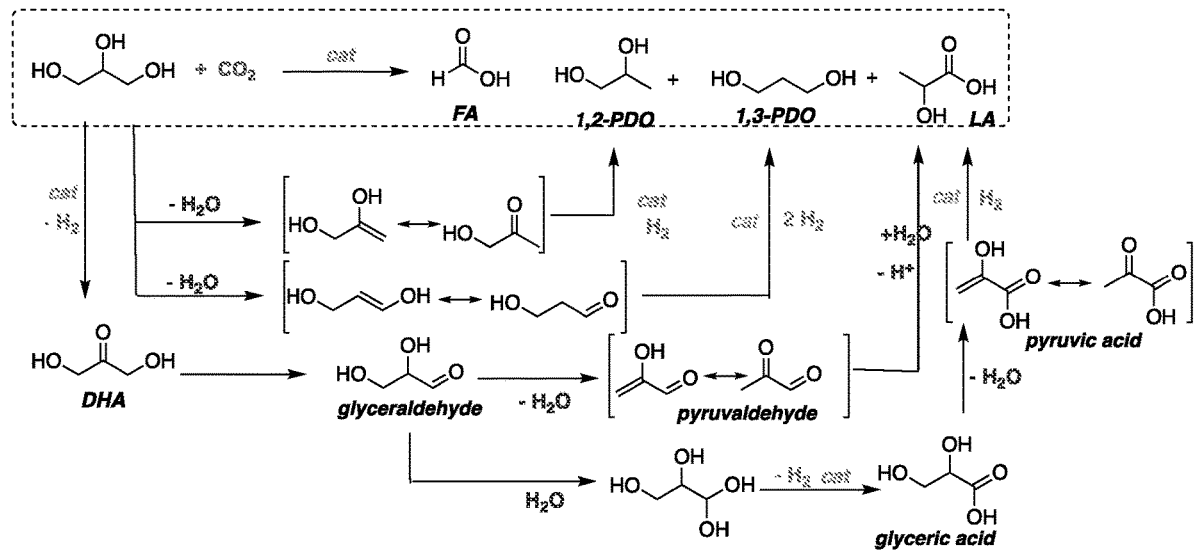
FIG. 1 is a graphical illustration of reaction pathways for the transformation of $CO_2$ and glycerol.

The following description of the embodiments is merely exemplary in nature and is in no way intended to limit the subject matter of the present disclosure, their application, or uses.

As used throughout, ranges are used as shorthand for describing each and every value that is within the range. Any value within the range can be selected as the terminus of the range. Unless otherwise specified, all percentages and amounts expressed herein and elsewhere in the specification should be understood to refer to percentages by weight.

For the purposes of this specification and appended claims, unless otherwise indicated, all numbers expressing quantities, percentages or proportions, and other numerical values used in the specification and claims, are to be understood as being modified in all instances by the term "about." The use of the term "about" applies to all numeric values, whether or not explicitly indicated. This term generally refers to a range of numbers that one of ordinary skill in the art would consider as a reasonable amount of deviation to the recited numeric values (i.e., having the equivalent function or result). For example, this term can be construed as including a deviation of ±10 percent, alternatively ±5 percent, alternatively ±1 percent, alternatively ±0.5 percent, and alternatively ±0.1 percent of the given numeric value provided such a deviation does not alter the end function or result of the value. Accordingly, unless indicated to the contrary, the numerical parameters set forth in this specification and attached claims are approximations that can vary depending upon the desired properties sought to be obtained by the present invention.

It is noted that, as used in this specification and the appended claims, the singular forms "a," "an," and "the," include plural references unless expressly and unequivocally limited to one referent. As used herein, the term "include" and its grammatical variants are intended to be non-limiting, such that recitation of items in a list is not to the exclusion of other like items that can be substituted or added to the listed items. For example, as used in this specification and the following claims, the terms "comprise" (as well as forms, derivatives, or variations thereof, such as "comprising" and "comprises"), "include" (as well as forms, derivatives, or variations thereof, such as "including" and "includes") and "has" (as well as forms, derivatives, or variations thereof, such as "having" and "have") are inclusive (i.e., open-ended) and do not exclude additional elements or steps. Accordingly, these terms are intended to not only cover the recited element(s) or step(s), but may also include other elements or steps not expressly recited. Furthermore, as used herein, the use of the terms "a" or "an" when used in conjunction with an element may mean "one," but it is also consistent with the meaning of "one or more," "at least one," and "one or more than one." Therefore, an element preceded by "a" or "an" does not, without more constraints, preclude the existence of additional identical elements.

The present invention relates to catalysts for the transformation of any one of carbon dioxide ($CO_2$), carbonate salts, or bicarbonate salts and glycerol to formic acid and lactic acid. The catalysts may be water soluble iridium (Ir) and/or ruthenium (Ru) N-heterocyclic carbene complexes, as homogeneous catalysts, or Ir and/or Ru N-heterocyclic carbene complexes bound to a solid substrate, as heterogeneous catalysts, for the transformation of any one of $CO_2$, carbonate salts or bicarbonate salts and glycerol to formic acid and lactic acid.

In accordance with various aspects of the present disclosure, homogeneous catalysts, for the transformation of carbon dioxide ($CO_2$) or carbonate/bicarbonate salts and glycerol to formic acid and lactic acid, can be described as having the following general chemical formula (I):

where
M is a transition metal;
NHC is an N-heterocyclic carbene ligand;
R is an alkyl or aryl group;
linker is a polar group;
L is a neutral ligand;
X is an anionic ligand;
a is an integer ranging from 1 to 3;
b is an integer ranging from 0 to 3; and
c is an integer ranging from 0 to 3.

In some instances, homogeneous catalysts according to chemical formula (I) can be in the form of a salt. In some instances, homogeneous catalysts according to chemical formula (I) can be in the form of a sodium (Na) or potassium (K) salt.

In accordance with various aspects of the present disclosure, the transition metal M can be, for example, any one of Fe, Ru, Os, Co, Rh, and Ir. The transition metal M can be in any suitable oxidation state. In some instances, it is preferred that M is $Ru^{2+}$. In other instances, it is preferred that M is $Ir^+$ or $Ir^{3+}$.

In accordance with various aspects of the present disclosure, the NHC group can be, for example, one formed my metalation of imidazolium salts derived from any one of 2,6-bis(1-imidazolyl)pyridine, 1,1'-methylenebis[imidazole], 2-(imidazol-1-yl)pyridine, 1-methylimidazole; N-trimethylsilylimidazole, 1-(2-chlorophenyl)imidazole, 1-(3-bromobenzyl)-1H-imidazole, 1-(3-chlorophenyl)imidazole, 1-(3-fluorophenyl)imidazole, 1-(4-chlorophenyl) imidazole, 1-(4-fluorophenyl)imidazole, 1-(m-tolyl)imidazole, 1-(3-aminopropyl)imidazole, 1-(diethoxymethyl) imidazole, 1H-imidazole-1-carboxylic acid-3-butenyl ester, 3-buten-2-yl 1H-imidazole-1-carboxylate, propargyl 1H-imidazole-1-carboxylate, 1-(p-toluenesulfonyl)imidazole, 1-(2-naphthoyl)imidazole, 1-(trifluoroacetyl)imidazole, 1-(tert-butyldimethyl silyl)imidazole, 1-(methyldithiocarbonyl)imidazole, 1-(trifluoromethanesulfonyl)imidazole, 1-(dimethyl sulfamoyl)imidazole, ethyl 1H-imidazole-1-carboxylate, methyl 1H-imidazole-1-carboxylate, 1-(4-methoxyphenyl)-1H-imidazole, 1-(11-mercaptoundecyl) imidazole, 1-[2-(trifluoromethyl)phenyl]imidazole, 1-[2-(3-bromophenoxy)ethyl]-1H-imidazole, and 1-(3-hydroxypropyl)-1H-imidazole.

In some instances, the NHC group is formed by metalation of imidazolium salts derived from 2,6-bis(1-imidazolyl) pyridine, 1,1'-methylenebis [imidazole], 2-(imidazol-1-yl) pyridine, and 1-methylimidazole.

In accordance with various aspects of the present disclosure, the R group can be any suitable unsubstituted or substituted $C_2$-$C_8$ alkyl group, $C_3$-$C_8$ cycloalkyl group, aryl group, polyaryl group, a polycyclic aromatic group, or any combination thereof. The R group can be, for example, any one of propyl, butyl, 1,8-naphthyl, phenyl (ortho, meta or para), and benzyl (ortho, meta or para, with $CH_2$ group bound to either of NHC or $SO_3$). In some instances, propyl or phenyl (para substituted) are preferred.

In accordance with various aspects of the present disclosure, the linker is a polar group, such as sulfonate, carboxylate, an acyl halide, hydroxylamine, or a trialkoxysilyl. In some instances, it is preferred that the linker be sulfonate.

In accordance with various aspects of the present disclosure, the neutral ligand L can be, for example, any one of carbon monoxide (CO), p-cymene, 1,5-cyclooctadiene (COD), 1,3-cyclohexadiene, 1,4-cyclohexadiene, ethylene, pyridine, a thiol, an alcohol, a phosphine, a trialkyl phosphine, a triaryl phosphine or phosphine oxide. In some instances, the neutral ligand L can be coordinated to metal and covalently bonded, either directly or indirectly, to the NHC group.

In accordance with various aspects of the present disclosure, the anionic ligand X can be, for example, any one of pentamethylcyclopentadienyl (Cp*), nitrosyl (NO), nitrile (CN), acetate, allyl, a halide such as Cl, Br or I, carbonate, triflate or trifluroacetate.

In accordance with various aspects of the present disclosure, for example, a homogeneous catalyst encompassed by chemical formula (I) can be described as having the chemical structure (I):

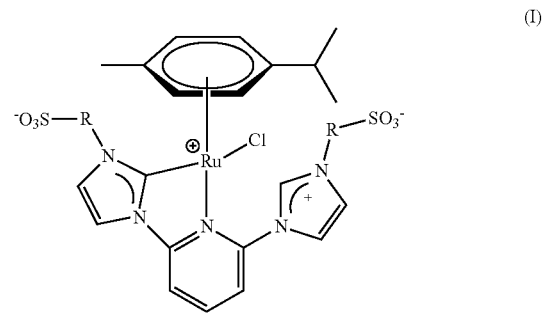

where R is a group as described above.

In accordance with various aspects of the present disclosure, for example, another homogeneous catalyst encompassed by chemical formula (I) can be described as having the chemical structure (II):

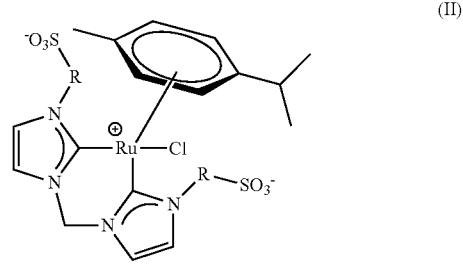

where R is a group as described above. Chemical structure (II) can be in the form of a Na or K salt.

In accordance with various aspects of the present disclosure, for example, yet another homogeneous catalyst encompassed by chemical formula (I) can be described as having the chemical structure (III):

(III)

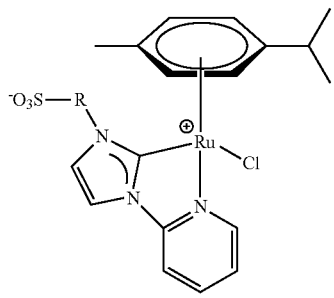

where R is a group as described above.

In accordance with various aspects of the present disclosure, for example, yet another homogeneous catalyst encompassed by chemical formula (I) can be described as having the chemical structure (IV):

(IV)

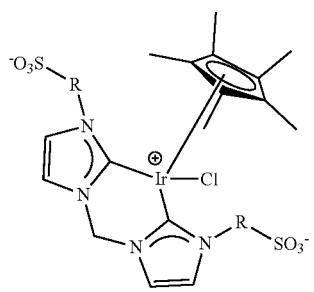

where R is a group as described above. Chemical structure (IV) can be in the form of a Na or K salt.

In accordance with various aspects of the present disclosure, for example, yet another homogeneous catalyst encompassed by chemical formula (I) can be described as having the chemical structure (V):

(V)

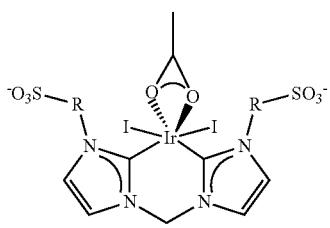

where R is a group as described above. Chemical structure (V) can be in the form of a Na or K salt.

In accordance with various aspects of the present disclosure, for example, yet another homogeneous catalyst encompassed by chemical formula (I) can be described as having the chemical structure (VI):

(VI)

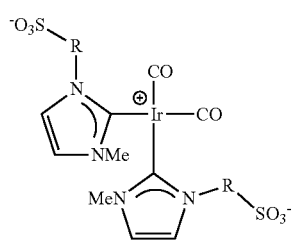

where R is a group as described above. Chemical structure (VI) can be in the form of a Na or K salt.

In accordance with various aspects of the present disclosure, for example, yet another homogeneous catalyst encompassed by chemical formula (I) can be described as having the chemical structure (VII):

(VII)

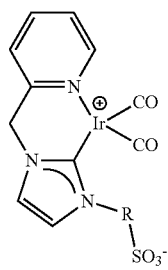

where R is a group as described above.

In accordance with various aspects of the present disclosure, for example, other homogeneous catalysts encompassed by chemical formula (I) can be described as including any one of chemical structures (VIII-XIV):

(VIII)

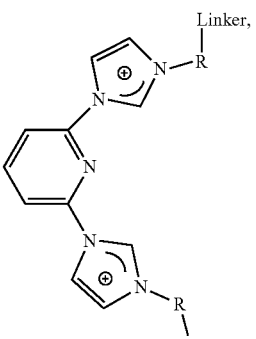

(IX)

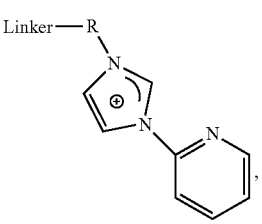

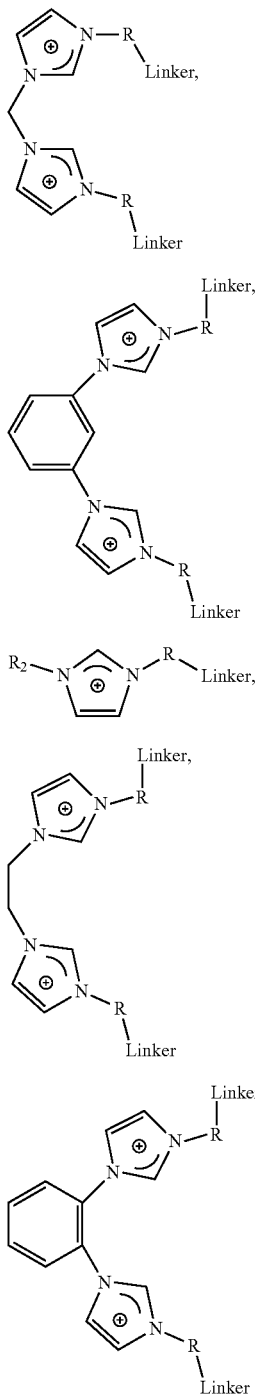

where the R and linker groups as described above.

In accordance with various aspects of the present disclosure, heterogeneous catalysts for the transformation of carbon dioxide ($CO_2$) or carbonate/bicarbonate salts and glycerol to formic acid and lactic acid can be synthesized by immobilizing a homogeneous catalyst according to chemical formula (I) onto a surface of a solid support. When a heterogeneous catalyst is used for the transformation of carbon dioxide ($CO_2$) or carbonate/bicarbonate salts and glycerol to formic acid and lactic acid, the immobilized homogeneous catalyst will serve as the catalytically active compound. In some instances, a homogeneous catalyst can be immobilized onto a surface of a solid support via ionic or Coulombic interactions. For example, this can occur when a negatively charged oxygen on a sulfonate group interacts with a Lewis acidic metal cation on the solid support surface. In some instances, a homogeneous catalyst can be immobilized onto a surface of a solid support via the formation of a covalent bond between a portion of the homogeneous catalyst and a solid support. For example, a covalent bond may be formed between a trimethoxysilane group and basic surface oxygen ions of a solid silica support. In some instances, bonding of a homogeneous catalyst onto a solid support can be accomplished indirectly by using a secondary linking compound which covalently binds to both of a portion of the homogeneous catalyst and the solid support. For example, a covalent bond may be formed between an acyl chloride moiety on the linker and an amine group previously covalently bonded (for example 3-aminopropyl trimethoxysilane) to a surface of a solid silica support.

In accordance with various aspects of the present disclosure, the solid support can be any suitable solid material having any one of a 3D structure (i.e., crystals or amorphous solid), a 2D structure (i.e., a single layer, or a plurality of layers with adjacent layers separated by an interstitial space), a 1D structure (i.e., rods, tubes, chains) or a 0D structure (i.e., separate molecules or spheres). The solid support can be non-porous or porous with pore diameters ranging from, for example, 1 nm to multiple micrometers (e.g., 2, 5, or 10 µm). In instances where the solid support is a 2D structure comprising a plurality of layers, the 2D structure can be exfoliated and/or have compounds (for example, $H_2O$) or ions (for example, $Li^+$, $CO_3^{2-}$, $Cr_2O_7^{2-}$) intercalated between adjacent layers. In some instances, non-porous solid supports can include, but are not limited to, glass substrates, a $TiO_2$-coated substrate, an indium tin oxide (ITO)-coated substrate, indium zinc oxide (IZO)-coated substrate an aluminum-doped zinc-oxide (AZO)-coated substrate, silica nanoparticles, buckminsterfullerene ($C_{60}$), $C_{540}$ fullerite, $C_{70}$, a nanosheet of graphene, graphene oxide or reduced graphene oxide, a nanosheet of boron nitride, and a silica or carbon nanorod. Porous supports can include, but are not limited to, porous silicates (for example, MCM-41 or SBA-15), porous aluminosilicates, silica nanotubes, activated carbon, carbon black, bone char, and single- or multiwalled carbon nanotubes, mixed metal oxides. Solid supports having a 2D structure comprising a plurality of layers can include, but are not limited to, graphite, exfoliated graphite, a clay (for example, montmorillonite, hectorite, saponite, illite, vermiculite, kaolinite, dickite and nacrite), a layered metal hydroxide or layered double hydroxide such as a hydrotalcite, manasseite, montmorillonite and hexagonal boron nitride (h-BN). In one or more embodiments of the present disclosure, the solid support is a hydrotalcite material (HT) and a mixed metal oxide. HTs include cationic sheets that are held together by interlayer anions and water molecules, forming a layered double hydroxide (LDH) structure. Naturally-occurring HTs have $Mg^{2+}$ and $Al^{3+}$ in the cationic sheets, but synthetic HTs can be prepared with other compatible transition metal ions such as, for example, Zn, Fe, Cr, Ni, Co, Ir, and Cu ions (with regard to Cu ions, hereinafter referred to as a "CuHT"), substituted in the cationic layer. The synthetic HTs share similar morphology but have tunable electronic properties, allowing optimization of activity and stability of the immobilized catalyst using the support properties. Mixed metal oxides are derived from hydrotalcite materials by calcination at temperatures above 400° C.

Homogeneous or heterogeneous catalysts in accordance with various aspects of the present disclosure can be used for the transformation of $CO_2$ and glycerol to formic acid and lactic acid. The formation of formaic acid and lactic acid in accordance with various aspects of the present disclosure can be described as occurring according to one or more reaction pathways as shown in FIG. 1. Without being bound to any particular theory, it is believed that one or more reaction pathways of FIG. 1 proceed in the same fashion, where carbonate salts are used as the carbon feedstock instead of $CO_2$, as $CO_2$ forms carbonate and bicarbonate in the presence of aqueous base.

In accordance with various aspects of the present disclosure, transformation of $CO_2$ and glycerol to formic acid and lactic acid can be performed under batch conditions or continuous flow conditions. As used herein, "batch conditions" means a reaction carried out in a vessel that is initially charged with the catalyst, glycerol and any one of $CO_2$, a carbonate salt, and a bicarbonate salt, and base (such as KOH), heated and allowed to react for a set amount of time, and then cooled to ambient conditions. As used herein "continuous flow conditions" means the glycerol and any one of $CO_2$, a carbonate salt, and a bicarbonate salt are continuously pumped into a preheated vessel, usually containing the catalyst, at the same rate the reacted substrate is removed from the vessel.

In accordance with various aspects of the present disclosure, transformation reactions under batch conditions can be performed in a pressurized reaction vessel. In some instances, the reaction vessel is a high temperature-pressure autoclave (Parr®, 4564 series) fitted with a glass insert, a standard mechanical agitator such a magnetically actuated stir bar or an impeller, and a liquid sampling tube. The reaction vessel can be of any suitable size (ranging from benchtop to large industrial scale) to perform the transformation of $CO_2$ or carbonate/bicarbonate and glycerol to formic acid and lactic acid. In instances where $CO_2$ is the carbon feedstock for formic acid and lactic acid formation, at least I) a reaction solution comprising a homogeneous or heterogeneous catalyst, glycerol, a base and water, and 2) $CO_2$ or a mixture of $CO_2$ and an inert gas, such as nitrogen or argon, will be added to the reaction vessel. Varying amounts of $CO_2$ will be dissolved within the reaction solution depending on the pressure of $CO_2$ within the reaction vessel and the concentration of the base. In instances where a carbonate or bicarbonate salt is the carbon feedstock for formic acid and lactic acid formation, at least I) a reaction solution comprising a homogeneous or heterogeneous catalyst, glycerol, a carbonate or bicarbonate salt, a base and water, and 2) an inert gas, such as nitrogen or argon, will be added to the reaction vessel. In other instances, batch reactions can be carried out in sealed reaction tubes in a scientific microwave reactor, such as CEM Discover or AntonPaar Monowave. Reactions performed under flow conditions can be carried out in a continuous flow reactor, comprising solvent pumps, a mass flow controller device that controls the delivery of gases, stainless steel tubing, a furnace and a liquid-gas separator.

When a transformation reaction is to be performed where $CO_2$ is the carbon feedstock for formic acid and lactic acid formation, the reaction vessel can be pressurized with $CO_2$ to pressures ranging from about 1 bar to about 100 bar, alternatively from about 5 bar to about 80 bar, alternatively from about 10 bar to about 60 bar, alternatively from about 20 bar to about 50 bar and alternatively from about 25 bar to about 50 bar. In some instances, when a transformation reaction is to be performed where $CO_2$ is the carbon feedstock, a mixture of $CO_2$ and an inert gas can be used. When a transformation reaction is to be performed where carbonate or bicarbonate is the carbon feedstock for formic acid and lactic acid formation, the reaction vessel can be pressurized with an inert gas, or a mixture of $CO_2$ and an inert gas, to pressures ranging from about 1 bar to about 100 bar, alternatively from about 5 bar to about 80 bar, alternatively from about 10 bar to about 60 bar, alternatively from about 20 bar to about 50 bar and alternatively from about 25 bar to about 50 bar.

In accordance with various aspects of the present disclosure, transformation reactions under continuous flow conditions, where $CO_2$ is the carbon feedstock for formic acid and lactic acid formation, can be conducted using a $CO_2$ pressure in a range as described above in combination with a continuous flow of $CO_2$ into and out of the reaction vessel. In such instances, the continuous flow of $CO_2$ can range from about 10 ml/min to about 50 ml/min, alternatively from about 15 ml/min to about 45 ml/min, alternatively from about 20 ml/min to about 40 ml/min, from about alternatively 25 ml/min to about 35 ml/min, and from alternatively from about 30 ml/min to about 35 ml/min.

In accordance with various aspects of the present disclosure, transformation reactions, whether under batch conditions or continuous flow conditions, can be performed at temperatures ranging from about 25° C. to about 400° C., alternatively from about 50° C. to about 350° C., alternatively from about 75° C. to about 300° C., alternatively from about 100° C. to about 250° C., alternatively from about 125° C. to about 250° C., and alternatively from about 150° C. to about 225° C.

In transformation reactions of the present disclosure, whether under batch conditions or continuous flow conditions, the glycerol can be added in an amount sufficient to achieve a glycerol concentration in the reaction solution ranging from about 1 molar (M) to about 15 M, alternatively about from 2 M to about 12 M, alternatively from about 3M to about 10 M, alternatively from about 4 M to about 8 M, alternatively from about 5 M to about 7 M, and alternatively about 6 M to about 7 M.

In transformation reactions of the present disclosure under batch conditions a homogeneous catalyst as described herein can be added to the reaction solution in an amount ranging from about 0.001 mol % to about 5 mol % relative to glycerol, alternatively from about 0.1 mol % to about 4 mol %, alternatively from about 0.25 mol % to about 3 mol %, alternatively from about 0.5 mol % to about 2 mol %, alternatively from about 0.75 mol % to about 1.5 mol %, alternatively from about 0.75 mol % to about 1.25 mol %, and alternatively about 1 mol %.

In transformation reactions of the present disclosure under batch conditions a heterogeneous catalyst as described herein can be added to the reaction solution in an amount sufficient to provide an amount of immobilized homogeneous catalyst ranging from about 0.001 mol % to about 5 mol % relative to glycerol, alternatively from about 0.1 mol % to about 4 mol %, alternatively from about 0.25 mol % to about 3 mol %, alternatively from about 0.5 mol % to about 2 mol %, alternatively from about 0.75 mol % to about 1.5 mol %, alternatively from about 0.75 mol % to about 1.25 mol %, and alternatively about 1 mol %. In transformation reactions of the present disclosure under flow conditions, a heterogeneous catalyst as described herein can be added to a frit that sits in a heated region of the stainless steel tubing in the amount of 5 mg to 500 mg.

In accordance with various aspects of the present disclosure, the base used in transformation reactions is KOH, NaOH, NaO$^t$Bu, KaO$^t$Bu, $K_2CO_3$ or $Na_2CO_3$. In some instances, other bases such as, for example, LiOH, Ca(OH)$_2$, Mg(OH)$_2$, Sr(OH)$_2$ and Ba(OH)$_2$ can be used. In transformation reactions of the present disclosure, whether under batch conditions or continuous flow conditions, the base can be added in an amount sufficient to give the reaction solution a base concentration ranging from about 0.1 molar (M) to about 14 M, alternatively from about 0.15 M to about 8 M, alternatively from about 0.20 to about 4 M, and alternatively from about 0.25 M to about 2 M.

In instances where a carbonate or bicarbonate salt is the carbon feedstock for formic acid and lactic acid formation, the carbonate or bicarbonate salt can be, for example, any one of lithium carbonate, lithium bicarbonate, sodium carbonate, sodium bicarbonate, sodium sesquicarbonate, potassium carbonate, potassium bicarbonate, magnesium carbonate, magnesium bicarbonate iron carbonate, calcium carbonate, strontium carbonate, and barium carbonate. In some instances, the use of potassium carbonate is preferred. Carbonate or bicarbonate salts can be added in an amount sufficient to give the reaction solution a carbonate/bicarbonate concentration ranging from about 0.1 molar (M) to about 5 M, alternatively from about 0.5 M to about 4 M, alternatively from about 1 to about 3 M, and alternatively from about 1.5 M to about 2.5 M.

EXAMPLES

Commercially available reagents were used without purification unless otherwise noted. [Ru(p-cymene)Cl$_2$]$_2$ was purchased from Acros Organics. Anhydrous solvents were dried using a solvent purification system (SPS MBraun) or 4 Å molecular sieves. Glycerol (>99%, Alfa Aesar) was dried over activated 4 Å molecular sieves. NMR spectra were recorded on an Agilent NMR spectrometer operating at 400 MHz. HPLC analysis was carried out using a Shimadzu Prominence-i (LC-2030C 3D) instrument equipped with a PDA detector. Catalyst synthesis was performed using standard air-free Schlenk techniques. In the Examples below, MeOH is methanol, MeCN is acetonitrile, DCM is methylene chloride, TMSOTf is trimethylsilyl trifluoromethanesulfonate, NaOAc is sodium acetate, $^i$PrOH is isopropanol, EtOH is ethanol, and Et$_2$O is diethyl ether.

Synthesis of Ligands

Ligand 1a. 2,6-Bis(1-imidazolyl)pyridine (0.538 g, 2.55 mmol) and 1,3-propane sultone (1.565 g, 12.8 mmol) were measured into a high pressure Pyrex tube. MeCN (10 mL) was added, and the vial was sealed and heated to 100° C. for 16 hours. After cooling to room temperature, the white precipitate was collected via filtration and washed with copious amounts of DCM and MeOH. Ligand 1a was collected as a white powder (1.011 g, 0.540 mmol, 87%). $^1$H NMR (400 MHz, D$_2$O) δ9.93 (s, 2H), 8.53-8.44 (m, 1H), 8.43-8.37 (m, 2H), 8.05 (dt, J=8.2, 1.1 Hz, 2H), 7.88 (dt, J=2.2, 1.3 Hz, 2H), 4.61 (t, J=7.1 Hz, 4H), 3.11-3.03 (m, 4H), 2.50 (p, J=7.2 Hz, 4H).

Ligand 2a. 1,1'P-Methylenebis[imidazole] (0.500 g, 3.38 mmol) and 1,3-propane sultone (2.083 g, 17.05 mmol) were measured into a high pressure Pyrex tube. MeCN (10 mL) was added, and the vial was sealed and heated to 100° C. for 16 hours. After cooling to room temperature the white precipitate formed was collected and washed thoroughly with MeOH and DCM before being dried in vacuo at room temperature. Ligand 2a was collected as a dry white powder (0.768 g, 1.96 mmol, 58%) $^1$H NMR (400 MHz, D$_2$O) δ7.84 (d, J=2.2 Hz, 2H), 7.75 (d, J=2.2 Hz, 2H), 6.75 (s, 2H), 4.49 (t, J=7.2 Hz, 4H), 2.99 (t, J=7.3 Hz, 5H), 2.39 (p, J=7.2 Hz, 4H).

Ligand 3a. 2-(Imidazol-1-yl)pyridine (0.4734 g, 3.26 mmol) and 1,2-propane sultone (0.5924 g, 0.485 mmol) were measured into a pyrex pressure tube with MeCN (7 mL). The tube was sealed and heated at 100° C. for 16 hours at which point a white precipitate is observed. After cooling to room temperature, the solid was collected by filtration and washed with three times with 10 mL CH$_2$Cl$_2$ and dried in vacuo at room temperature. Ligand 3a was recovered as a white solid (828 mg, 3.1 mmol, 94% yield). $^1$H NMR (400 MHz, D$_2$O) 6 9.65 (t, J=1.7 Hz, 1H), 8.61 (ddd, J=4.9, 1.8, 0.8 Hz, 1H), 8.20 (dd, J=2.2, 1.7 Hz, 1H), 8.17 (ddd, J=8.2, 7.6, 1.8 Hz, 1H), 7.85-7.79 (m, 2H), 7.65 (ddd, J=7.6, 5.0, 0.9 Hz, 1H), 4.55 (t, J=7.2 Hz, 2H), 3.07-2.99 (m, 2H), 2.50-2.39 (m, 2H). $^{13}$C NMR (101 MHz, D$_2$O) δ194.92, 149.18, 146.20, 140.89, 134.48, 125.48, 123.23, 120.00, 114.94, 48.47, 47.15, 24.92. HRMS(ESI/Q-TOF) m/z: [M+H]$^+$ Calcd for C$_{11}$H$_{14}$N$_3$O$_3$S 268.0756; Found 268.0759.

Ligand 6a. 1,3-Propane sultone (2.226 g, 18.23 mmol) was added to a 25 mL schlenk flask under a nitrogen atmosphere. 1-Methylimidazole (1.47 mL, 18.4 mmol) was added slowly at room temperature with constant stirring. After 5 minutes a white solid began to form and excess heat was produced. After 20 minutes the reaction mixture was completely solid. The solid was ground into a fine powder and washed with toluene (3×10 mL) and ether (3×10 mL) leaving ligand 6a as a white powder (2.836 g, 13.88 mmol, 76%). $^1$H NMR (400 MHz, D$_2$O) δ8.79 (s, 1H), 7.56 (s, 1H), 7.48 (s, 1H), 4.40 (t, J=7.1 Hz, 2H), 3.93 (d, J=0.7 Hz, 3H), 2.96 (dd, J=8.2, 6.7 Hz, 2H), 2.41-2.30 (m, 2H).

Ligand 6b. In a nitrogen atmosphere, 4-fluorobenzenesulfonyl chloride (1.109 g, 5.7 mmol) was dissolved in 40 mL dry MeCN. 1-Methylimidazole (1.8 mL, 22.5 mmol) and TMSOTf (2 mL, 11.0 mmol) were added via syringe and the mixture was heated to reflux for 48 h under nitrogen, during which the color changed from clear to red and a white precipitate formed. After cooling to room temperature, the precipitate was collected, washed with MeCN (3×10 mL) and DCM (3×10 mL) and dried in vacuo leaving ligand 6b as a white powder (205 mg, 0.862 mmol, 15%). $^1$H NMR (400 MHz, D$_2$O) δ9.32 (s, 1H), 8.07-8.00 (m, 2H), 7.96 (t, J=1.9 Hz, 1H), 7.81-7.74 (m, 2H), 7.68 (t, J=1.9 Hz, 1H), 4.06 (s, 3H).

Synthesis of Homogeneous Catalysts

Catalyst 1a. Ligand 1a (24 mg, 0.27 mmol) was dissolved in 16 mL MeOH/3 mL H$_2$O (solvents degassed) and Ag$_2$O (63 mg, 0.27 mmol) was added in the darkness to form a suspension. The suspension was stirred at 50° C. for 60 min, then NaCl (16 mg, 0.27 mmol) was added and the resulting suspension stirred vigorously for 15 min, after which it was filtered and transferred to a solution of [Ru(p-cymene)Cl$_2$]$_2$ (98 mg, 0.16 mmol) in 10 mL H$_2$O. After 1 hour at room temperature, the suspension was filtered and the solvent was removed in vacuo at 50° C. The resulting dark residue was then extracted with MeOH (three times with 10 mL) and filtered. The orange solution was then reduced to a volume of 5 mL and Et$_2$O added until the precipitation of an orange solid was observed. This procedure was repeated if still some unreacted ligand was visible in crude proton NMR spectroscopy. The solvent was decanted and the residue washed with $Et_2O$ (three times with 10 mL) and dried in vacuo to yield Catalyst 1a as an orange powder (46 mg, 0.063 mmol; 30%). $^1H$ NMR ($d^6$-DMSO, 400 MHz): δ=8.43 (d, J=0.9 Hz, 1H), 8.35 (t, J=1.0 Hz, 1H), 8.18 (d, J=0.8 Hz, 1H), 8.15 (dd, J=8.5, 1.0 Hz, 1H), 8.05 (d, J=0.8 Hz, 1H), 7.75 (dd, J=2.4, 0.8 Hz, 1H), 7.72 (d, J=6.1 Hz, 1H), 6.12 (brs, 1H), 5.54 (d, J=6.1 Hz, 1H,), 5.43 (d, J=6.1 Hz, 1H), 4.75 (brs, 1H), 4.62-4.32 (m, 4H), 2.90-2.68 (m 4H), 2.41-2.18 (m, 4H), 2.10-2.00 (m, 1H), 1.97 (s, 3H), 0.65 ppm (d, J=6.8 Hz, 6H). $^{13}C$-NMR (DMSO, 100 MHz): δ=184.6, 153.9, 150.7, 146.3, 126.6, 126.2, 124.8, 123.0, 119.9, 116.2, 88.1, 50.0, 49.3, 48.1, 47.5, 30.6, 25.7, 25.1, 22.0, 21.6, 18.6 ppm.

Catalyst 2a. Methylenebis-[N,N'(propanesulfonate)imidazolium] (Ligand 2a, 80 mg, 0.20 mmol) was dissolved in 20 mL degassed $H_2O$ and $Ag_2O$ (46 mg, 0.20 mmol) added in the darkness. The suspension was stirred at 50° C. for 90 min, then NaCl (12 mg, 0.20 mmol) was added and the resulting suspension stirred vigorously for 15 min, after which it was transferred to a solution of $[Ru(p\text{-}cymene)Cl_2]_2$ (61 mg, 0.10 mmol) in 15 mL $H_2O$. After 1 hour at 50° C., the solvent was removed in vacuo and the resulting dark residue extracted with MeOH (3×10 mL) and filtered over a pad of silica. The yellow solution was then reduced to 5 mL and $Et_2O$ added until the precipitation of a yellow solid was observed. The solvent was decanted and the residue washed with $Et_2O$ (3×10 mL) and dried in vacuo to yield Catalyst 2a as a yellow powder (95 mg; 0.143 mmol; 71%). $^1H$-NMR ($D_2O$, 400 MHz): δ7.51 (dd, J=0.7 Hz, 2H), 7.49 (dd, J=0.7 Hz, 2H), 6.22-6.15 (m, 1H), 5.94 (d, J=6.2 Hz, 2H), 5.86 (d, J=6.2 Hz, 2H), 5.57 (d, J=13.1 Hz, 1H), 4.64-4.52 (m, 2H), 4.50-4.38 (m, 2H), 3.14-2.97 (m, 4H), 2.48-2.24 (m, 6H), 2.18 (s, 3H), 1.04 (dd, J=6.8, 0.7 Hz, 6H). $^{13}C$-NMR ($D_2O$, 100 MHz): δ=173.4, 122.3, 121.7, 106.8, 105.3, 92.1, 86.7, 61.7, 48.9, 48.3, 31.8, 25.8, 21.9, 17.9 ppm.

Catalyst 3a. In a flask, ligand 3a (75 mg, 0.28 mmol) was dissolved in a degassed solution of 16 mL MeOH and 3 mL $H_2O$. The flask was wrapped in foil and $Ag_2O$ (65 mg, 0.28 mmol) was added in darkness, and the solution stirred at 50° C. for 90 minutes. A solution of NaCl (35 mg, 0.60 mmol) in 1 mL $H_2O$ was added and the solution stirred for another 15 minutes. The silver solution was then filtered and transferred to a solution of $[Ru(p\text{-}cymene)Cl_2]_2$ (100 mg, 0.16 mmol) in 15 mL $H_2O$ and stirred at room temperature overnight. The solution was filtered, and the filtrate dried in vacuo at 50° C. 50 mL MeCN was added to the crude product, stirred for 1 h at room temperature and filtered over celite. The clear yellow filtrate was dried, dissolved in a minimum amount of MeOH, and transferred to a silica column. Elution with 800 mL Acetone/MeOH (80/20) and 400 mL Acetone/MeOH (50/50) afforded a bright orange band. Removal of the solvent in vacuo afforded Catalyst 3a as a highly hygroscopic orange solid (45 mg, 0.0837 mmol, 30% yield). $^1H$ NMR (400 MHz, $CD_3OD$) δ 9.32 (ddd, J=5.8, 1.5, 0.7 Hz, 1H), 8.24-8.17 (m, 2H), 8.02 (ddd, J=8.3, 1.2, 0.7 Hz, 1H), 7.78 (d, J=2.3 Hz, 1H), 7.52 (ddd, J=7.5, 5.8, 1.3 Hz, 1H), 6.47 (dd, J=6.1, 1.3 Hz, 1H), 6.31 (dd, J=6.3, 1.3 Hz, 1H), 6.13 (dd, J=6.4, 1.3 Hz, 1H), 5.88 (dd, J=6.1, 1.4 Hz, 1H), 4.85-4.78 (m, 1H), 4.72 (ddd, J=13.8, 10.6, 5.8 Hz, 1H), 3.06 (dt, J=7.5, 5.1 Hz, 2H), 2.65-2.54 (m, 1H), 2.43 (p, J=7.0 Hz, 2H), 2.27 (s, 3H), 0.98 (dd, J=6.9, 3.8 Hz, 6H). $^{13}C$ NMR (101 MHz, $CD_3OD$) δ185.30, 156.75, 153.38, 142.66, 126.19, 124.25, 118.06, 113.51, 92.80, 92.40, 88.33, 82.60, 51.35, 49.29, 32.48, 27.77, 22.90, 22.52, 19.32. HRMS(ESI/Q-TOF) m/z: $[M+H]^+$ Calcd for $C_{21}H_{27}N_3O_3SRuCl$ 538.0505; Found 538.0504.

Catalyst 4a. Methylenebis-[N,N'(propanesulfonate)imidazolium] (Ligand 2a, 44.6 mg, 0.113 mmol) was dissolved in 10 mL degassed $H_2O$. $Ag_2O$ (24.8 mg, 0.107 mmol) was added to this solution which was heated at 50° C. for 90 minutes in darkness. A solution of NaCl (7.1 mg, 0.121 mmol) in 0.5 mL degassed $H_2O$ was added to the silver solution and stirred for a further 15 minutes. In a 25 mL Schlenk flask, under a nitrogen atmosphere $[IrCp*Cl_2]_2$ (45.3 mg, 0.057 mmol) was dissolved in 7 mL of degassed $H_2O$/DMSO (1:1 v:v). Under a flow of nitrogen the silver solution was transferred to the $[IrCp*Cl_2]_2$ which immediately became cloudy. After stirring overnight at room temperature the solvent was removed at 50° C. under vacuum. The orange residue was washed with MeOH (3×5 mL) and filtered over Celite. The filtrate was reduced in volume to 3 mL, where addition of $Et_2O$ produced a yellow precipitate. Washing three times more with $Et_2O$ and drying in vacuo produced Catalyst 4a as a yellow solid (69.35 mg, 0.0893 mmol, 79%). $^1H$ NMR (400 MHz, Methanol-d4) δ7.53 (d, J=2.1 Hz, 2H), 7.49 (d, J=2.1 Hz, 2H), 6.23 (d, J=13.1 Hz, 1H), 5.59 (d, J=13.0 Hz, 1H), 4.36-4.23 (m, 5H), 2.92-2.85 (m, 5H), 2.43-2.29 (m, 3H), 2.17 (ddt, J=14.7, 13.3, 7.2 Hz, 3H), 1.81 (s, 15H). $^{13}C$ NMR (101 MHz, $CD_3OD$) δ150.94, 121.45, 121.09, 93.18, 61.65, 48.72, 48.39, 26.71, 8.04.

Catalyst 5a. A mixture of methylenebis-[N,N'(propanesulfonate)imidazolium] (Ligand 2a, 78 mg, 0.2 mmol), $[Ir(COD)OMe]_2$ (67 mg, 0.1 mmol), KI (100 mg, 0.6 mmol), and NaOAc (65 mg, 0.8 mmol) was stirred in MeOH at reflux temperature for 16 h. The suspension was filtered through Celite, and after drying under vacuum; the solid was washed with $CH_2Cl_2$ (40 mL) and acetone (40 mL). The solid was purified by chromatography. Elution with MeOH/acetone (1:1, 40 mL) afforded the separation of a yellow band that contained the compound. Catalyst 5a was obtained as a yellow solid by precipitation from MeOH/iPrOH (yield: 134.37 mg, 38%). $^1H$ NMR ($CD_3OD$, 400 MHz): δ=7.41 (d, J=2.2 Hz, 2H), 7.31 (d, J=2.2 Hz, 2H), 6.26 (s, 2H) 4.56 (t, J=7.3 Hz, 4H), 2.96 (t, J=7.3 Hz, 4H), 2.42-2.24 (m, 4H), 1.93 (s, 3H). $^{13}C$-NMR (DMSO, 100 MHz): δ=176.4, 123.7, 122.1, 120.5, 48.3, 47.8, 26.9, 24.5 ppm.

Catalyst 6a. The synthesis of Catalyst 6a was performed according the reaction scheme below:

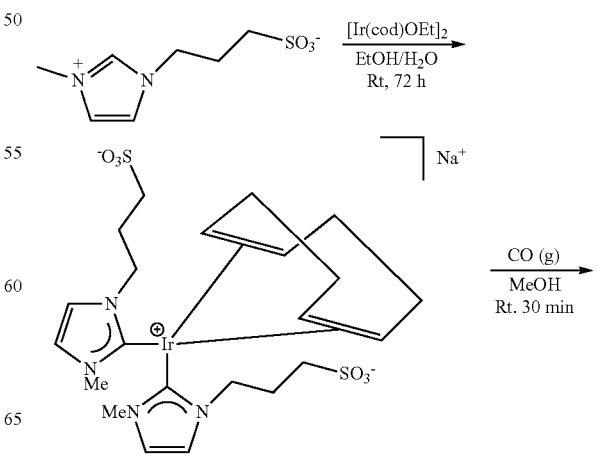

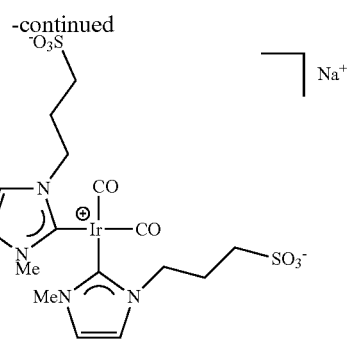

Under a nitrogen atmosphere [Ir(cod)Cl]$_2$ (66 mg, 0.098 mmol) was dissolved in 8 mL degassed EtOH (200 proof). A solution of NaH (25 mg, 60 wt % in mineral oil) in 2 mL EtOH was added dropwise, the solution quickly from orange to yellow and was stirred for 30 minutes at 25° C. A suspension of the Ligand 6a (0.37 mmol) in 3 mL EtOH and 0.5 mL H$_2$O, slowly added to the iridium solution via syringe and stirred at 25° C. for 72 hours. The solvent was then removed under reduced pressure and the crude product re-dissolved in a minimum amount of MeOH (3 mL). Addition of Et$_2$O afforded a precipitate, which was collected, washed three times more with Et$_2$O and dried under vacuum.

Complex 6a-cod was recovered as a hygroscopic red solid (78 mg, 0.106 mmol, 57% yield). $^1$H NMR (400 MHz, CD$_3$OD) δ7.26 (dd, J=14.0, 2.0 Hz, 2H), 7.17 (dd, J=10.3, 2.0 Hz, 2H), 4.57-4.45 (m, 2H), 4.24-4.12 (m, 2H), 4.07 (m, 1H), 4.05 (s, 6H), 3.89 (m, 1H), 3.73-3.65 (m, 2H), 2.99-2.89 (m, 4H), 2.50-2.41 (m, 2H), 2.35-2.24 (m, 2H), 2.24-2.14 (m, 4H), 2.05-1.95 (p, J=7.5 Hz, 2H), 1.91-1.71 (m, 2H). $^{13}$C NMR (101 MHz, CD$_3$OD) δ176.60, 161.59, 123.12, 120.66, 109.99, 77.36, 74.54, 49.10, 37.40, 32.01, 29.46, 26.15. Complex 6a-cod (54 mg, 0.073 mmol) was dissolved in 10 mL degassed MeOH, and the system was flushed with N$_2$ for 10 minutes. CO(g) was bubbled through the solution at room temperature for 90 minutes, and the solution changed from orange to yellow in color. The solvent was reduced to about 2 mL in vacuo at room temperature, at which point addition of Et$_2$O afforded the formation of a yellow precipitate. The solid was washed 3×5 mL further with Et$_2$O and dried in vacuo at room temperature to yield Catalyst 6a as a yellow solid (35 mg, 0.051 mmol, 69% yield). $^1$H NMR (400 MHz, CD$_3$OD) δ7.45 (d, J=2.0 Hz, 2H), 7.41 (d, J=2.0 Hz, 2H), 4.06 (t, J=7.6 Hz, 4H), 3.98 (s, 6H), 2.78 (t, J=7.2 Hz, 4H), 2.13 (m, 4H). $^{13}$C NMR (101 MHz, CD$_3$OD) δ179.88, 166.83, 124.26, 122.46, 49.33, 47.71, 37.74, 26.28. HRMS(ESI/Q-TOF) m/z: [M—Na]$^+$ Calcd for C$_{16}$H$_{22}$N$_4$S$_2$O$_8$Ir 655.0508; Found 655.0505.

In some instances, homogeneous catalysts similar to Catalyst 6a but having any one of carboxylate, an acyl halide, hydroxylamine, or a trialkoxysilyl in place of the sulfonate groups, can be synthesized using similar conditions. In some instances, such as when Ligand 6a has a trialkoxysilyl group in place of the sulfonate group, the use of an organic solvent may be required to avoid hydrolysis of said trialkoxysilyl group.

Catalyst 6b. The synthesis of Catalyst 6b was performed according the reaction scheme below:

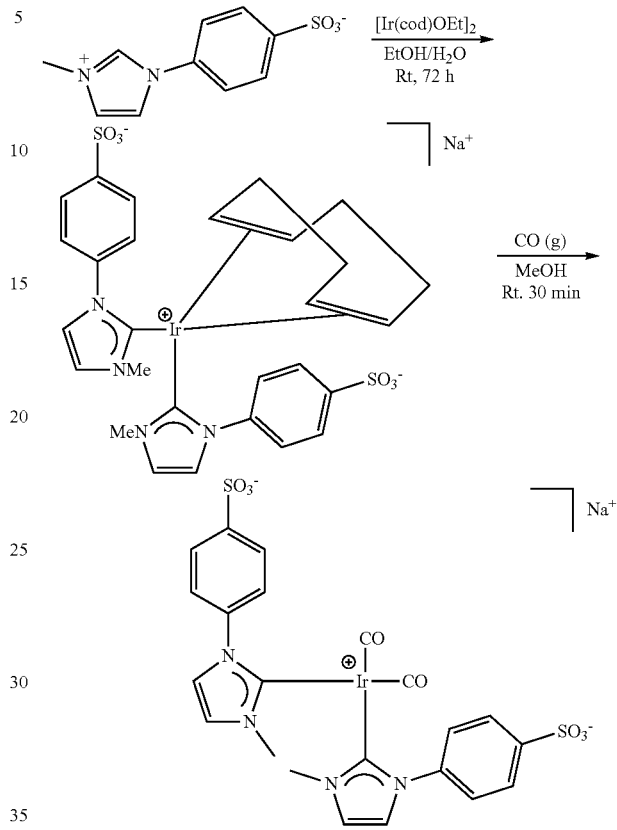

Under a nitrogen atmosphere [Ir(cod)Cl]$_2$ (66 mg, 0.098 mmol) was dissolved in 8 mL degassed EtOH (200 proof). A solution of NaH (25 mg, 60 wt % in mineral oil) in 2 mL EtOH was added dropwise, the solution quickly from orange to yellow and was stirred for 30 minutes at 25° C. A suspension of ligand 6b (0.37 mmol) in 3 mL EtOH and 0.5 mL H$_2$O, slowly added to the iridium solution via syringe and stirred at 25° C. for 72 hours. The solvent was then removed under reduced pressure and the crude product re-dissolved in a minimum amount of MeOH (3 mL). Addition of Et$_2$O afforded a precipitate, which was collected, washed three times more with Et$_2$O and dried under vacuum.

Complex 6b-cod was recovered as a bright red solid (69 mg, 0.086 mmol, 53% yield). $^1$H NMR (400 MHz, CD$_3$OD) δ8.02-7.97 (m, 4H), 7.37-7.32 (m, 4H), 7.24 (d, J=2.0 Hz, 2H), 7.14 (d, J=2.0 Hz, 2H), 4.78-4.70 (m, 2H), 3.61 (q, J=7.7 Hz, 2H), 3.22 (s, 6H), 2.51 2.38 (m, 2H), 2.28 (dd, J=15.2, 7.8 Hz, 2H), 2.17-2.05 (m, 2H), 1.69 (td, J=14.4, 7.3 Hz, 2H). $^{13}$C NMR (101 MHz, CD$_3$OD) δ177.58, 147.47, 142.61, 128.28, 127.14, 124.30, 124.25, 80.73, 73.91, 38.00, 35.94, 28.26. Complex 6b-cod (69 mg, 0.086 mmol) was dissolved in 10 mL degassed MeOH, and the system was flushed with N$_2$ for 10 minutes. CO(g) was bubbled through the solution at room temperature for 90 minutes, and a solution changed from red/orange to an orange/yellow color. The solvent was reduced to about 2 mL in vacuo, after which Et$_2$O was added until a yellow precipitate was formed. The solid was washed 3 times with Et$_2$O and dried in vacuo to yield Catalyst 6b as a yellow solid (36 mg, 0.047 mmol, 54% yield). $^1$H NMR (400 MHz, D$_2$O) δ7.90-7.85 (m, 4H), 7.50-7.46 (m, 4H), 7.24 (d, J=2.0 Hz, 2H), 7.00 (d, J=2.0 Hz, 2H), 3.44 (s, 6H). $^{13}$C NMR (101 MHz, D$_2$O) δ179.49, 168.73, 163.16, 142.84, 140.92, 126.64, 125.27, 123.95, 122.39, 38.31. HRMS(ESI/Q-TOF) m/z: [M+H]$^+$ Calcd for C$_{22}$H$_{19}$N$_4$S$_2$O$_8$IrNa 747.0177; Found 747.0155.

In some instances, homogeneous catalysts similar to Catalyst 6b but having any one of carboxylate, an acyl halide, hydroxylamine, or a trialkoxysilyl in place of the sulfonate groups, can be synthesized using similar conditions. In some instances, such as when Ligand 6b has a trialkoxysilyl group in place of the sulfonate group, the use of an organic solvent may be required to avoid hydrolysis of said trialkoxysilyl group.

Transformation Reactions

Transformation reactions were carried out in a high temperature-pressure autoclave (Parr®, 4564 series) fitted with a glass insert, standard mechanical agitator, and liquid sampling tube. The glass insert was loaded with catalyst, 25 mL of aqueous KOH (of desired concentration) and 25 mL of glycerol. The glass insert was then placed into the autoclave. The autoclave was sealed, and the stirrer turned on and set to 75% power. The autoclave was purged 5 times with CO$_2$ (Praxair, industrial grade) and pressurized to 10 bar. When the reaction reached the desired temperature, the pressure was adjusted to the desired operating conditions, typically 26 or 46 bar. Reactions with carbonate were carried out in a similar manner, but pressurized with nitrogen instead of CO$_2$.

Reactions aliquots were obtained periodically for analysis, maintaining the designated CO$_2$ pressure. Reaction aliquots were analyzed by HPLC and NMR using 2,2,3,3-d (4)-3-(trimethylsilyl)propionic acid sodium salt as a standard. HPLC was performed using a Shimadzu Prominence-i (LC-2030C 3D) instrument equipped with a PDA detector using a mobile phase of 0.005 M H$_2$SO$_4$ with a flow rate of 0.44 mL/min at 35° C. Samples for quantification of lactic acid (LA), formic acid (FA) and 1,2-propanediol (1,2-PDO) were prepared by adding a 1-mL aliquot of sample to 0.22 mL of 5 M H$_2$SO$_4$ and filtering with a syringe filter. The PDA detector scanned the range of 190-800 nm, affording traces at 190, 218, 254, and 284 nm for analysis. The 190-nm wavelength trace included glycerol and all the desired products, while the 218-nm trace excluded glycerol and 1,2-PDO. Typical HPLC trace and PDA chromatograms exhibited retention times of 28.7, 29.5, 30.5, and 36 min for LA, glycerol, FA and 1,2-PDO respectively.

Control reaction without catalyst afford no appreciable conversion of glycerol, while control reactions without CO$_2$ or carbonate afford only lactate. Esters of glycerol lactate or formate were not observed under basic conditions.

Optimization Testing for CO$_2$ and Glycerol Transformation using Homogeneous Catalyst 1a. To identify optimal reaction conditions for catalyst screening the activity of Catalyst 1a (5 mg) with 6.85 M glycerol (1:1 water:glycerol) was examined using different temperatures, pressures of CO$_2$, and base (KOH) concentrations, the results of which are shown in Table 1. All experiments in Table 1 had a total volume of 50 mL.

TABLE 1

| Exp. | Temp (° C.) | Pressure (bar) | [KOH] (M) | TON in 1 h LA | TON in 1 h FA | TON in 24 h LA | TON in 24 h FA | Final conc. (mM) LA | Final conc. (mM) FA |
|---|---|---|---|---|---|---|---|---|---|
| 1 | 150 | 46 | 0.25 | 141 | 71 | 312 | 110 | 51.8 | 18.0 |
| 2 | 225 | 46 | 0.25 | 352 | 82 | 3297 | 280 | 328 | 27.9 |
| 3 | 150 | 46 | 1 | 28 | 28 | 360 | 330 | 56.2 | 49.8 |
| 4 | 150 | 46 | 2 | 58 | 57 | 356 | 329 | 59.4 | 55.1 |
| 5 | 150 | 46 | 0 | 0 | 0 | 0 | 0 | 0 | 20 |
| 6 | 225 | 46 | 0 | 88 | 26 | 206 | 141 | 60.4 | 48.6 |
| 7 | 150 | 26 | 2 | 38 | 38 | 632 | 586 | 95.5 | 86.3 |
| 8 | 180 | 26 | 2 | 520 | 348 | 1685 | 1065 | 262 | 166 |

Figure 2:
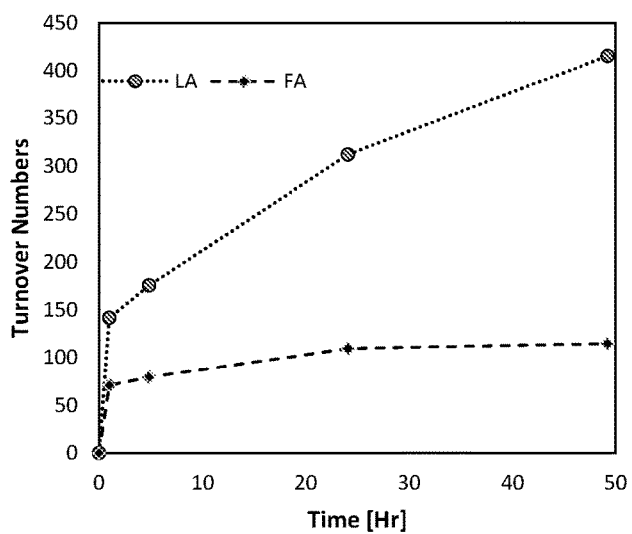
FIG. 2 is a graph showing the time course for production of formic acid (FA) and lactic acid (LA) from the reaction of $CO_2$ and glycerol using Catalyst 1a, 46 bar $CO_2$, 6.85 M glycerol, and 0.25 M KOH at 150° C.
Figure 3:
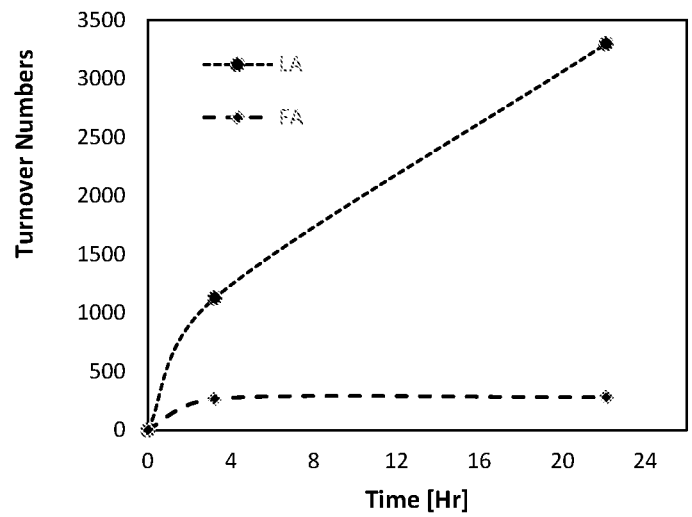
FIG. 3 is a graph showing the time course for production of FA and LA from the reaction of $CO_2$ and glycerol using Catalyst 1a, 46 bar $CO_2$, 6.85 M glycerol, and 0.25 M KOH at 225° C.
Figure 4:
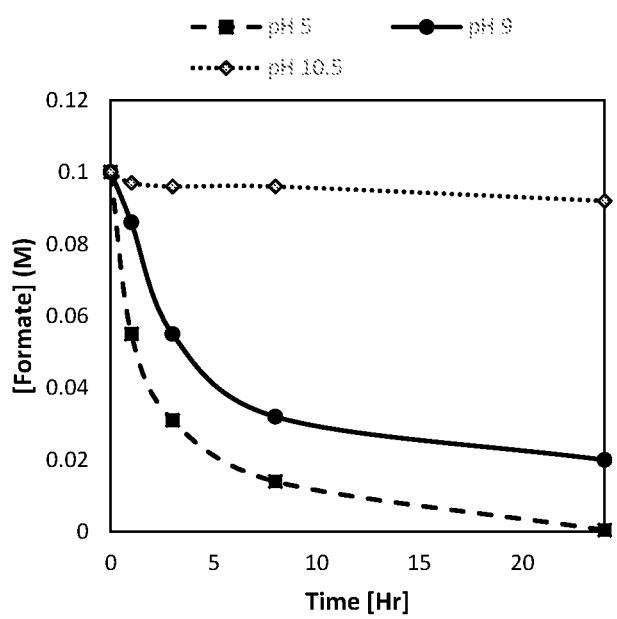
FIG. 4 is a graph showing the time course for decomposition of formic acid to $CO_2$ and $H_2$ in aqueous medium at pH=5, 9 or 10.5, using Catalyst 1a at 150° C. (0.15 mM Catalyst 1a, 0.10 M formic acid, KOH(aq) to adjust pH, 50 mL total volume of water)

The turnovers of lactate and formate observed with Catalyst 1a were found to depend on the temperature and availability of base. In the absence of base, no products are observed from a reaction at 150° C. However, reactions with Catalyst 1a (0.15 mM), 1 M KOH, 1:1 glycerol:water at 46 bar CO$_2$ and 150° C. afford 330 turnovers in 24 h, equivalent to ~50 mM of formate and lactate (Table 1, Experiment 3). Further increase in reaction time afforded more lactic but no more formic acid. Doubling the base concentration (2 M KOH) affords similar TONs in 24 hours, but the initial activity (TON at t=1 hr) is doubled (Table 1, Experiment 4). This is attributed to the fact that the initial KOH concentration is higher for the reaction with 2 M KOH, resulting in higher initial rate. However, as the vessel is pressurized, the KOH solubility reaches saturation, which results in a similar effective base concentration in both reactions. When KOH concentration is decreased to 0.25 M, the reaction still affords ~50 mM lactate, but significantly less formate (18 mM, Table 1, Experiment 1), and a drop in pH to 6.9 is observed after 24 hr. FIGS. 2 and 3 are graphs showing the formation (in TONs) of lactic acid and formic acid at 46 bar CO$_2$ using 0.25 M KOH and temperatures of 150° C. (FIG. 2) and 225° C. (FIG. 3). When performed at 150° C., the 1-hr TONs are 141 and 71 respectively for lactic acid and formic acid, with lactic concentration steadily increasing and that of formic acid becoming steady (FIG. 2). When performed at 225° C. the 1-hr TONs for lactic acid and formic acid are markedly higher. Without being bound to any particular theory, it is believed that this observation was due to competing CO$_2$ hydrogenation and formic acid dehydrogenation at the lower pH. Indeed, experiments with Catalyst 1a at 150° C. confirm that the catalyst has pH-dependent activity for decomposition of formic acid/formate to CO$_2$ and H$_2$ (FIG. 4).

Figure 5:
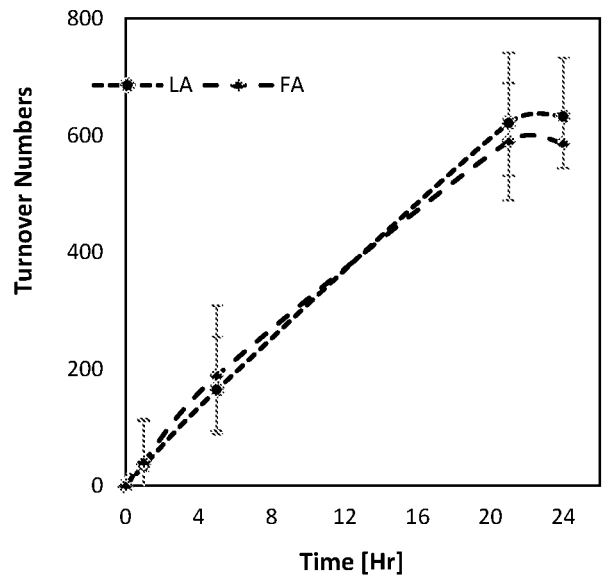
FIG. 5 is a graph showing the time course for production of formic acid and lactic acid from the reaction of $CO_2$ and glycerol using Catalyst 1a using $pCO_2$ 26 bar, 6.85 M aqueous glycerol and 2.00 M KOH at 150° C. (error bars based on average of two replicates)
Figure 6:
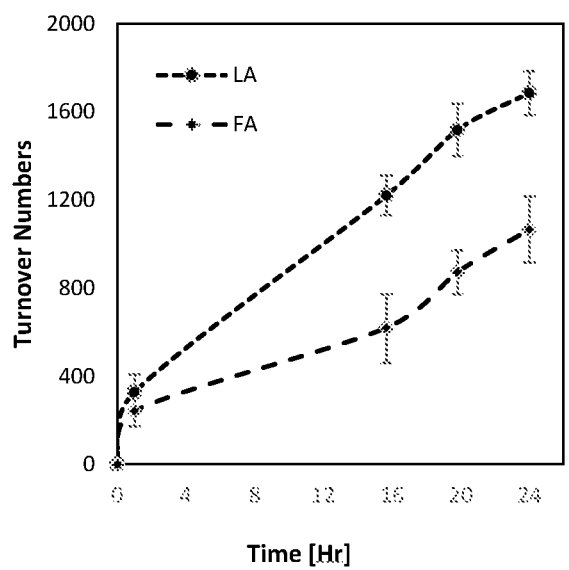
FIG. 6 is a graph showing the time course for production of formic acid and lactic acid from the reaction of $CO_2$ and glycerol using Catalyst 1a using $pCO_2$ 26 bar, 6.85 M aqueous glycerol and 2.00 M KOH at 180° C. (error bars based on average of two replicates)
Figure 7:
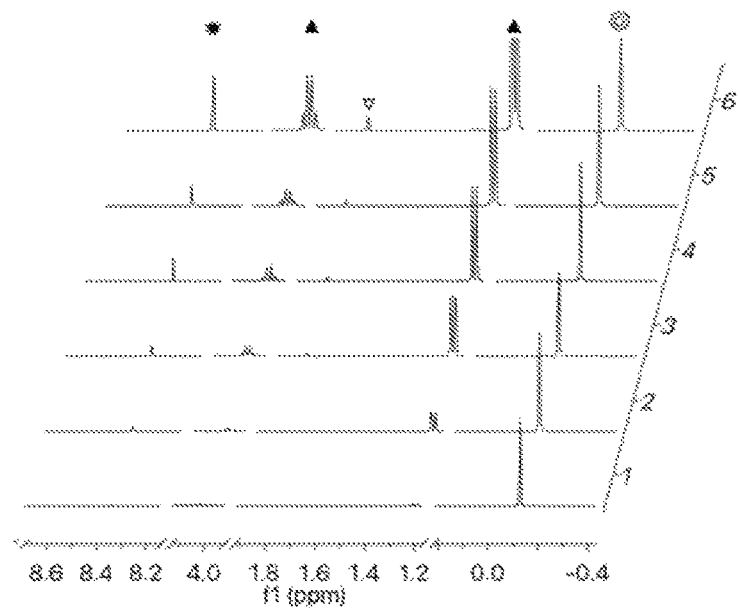
FIG. 7 is a graph showing sections of $^1H$ NMR spectra corresponding to (1) t=0 h, (2) t=1 h, (3) t=8 h, (3) t=15 h, (4) t=19 h, (5) t=24 h and (6) t=86 h for reaction of $CO_2$ and glycerol using Catalyst 1a ($pCO_2$ 26 Bar, 6.85 M aqueous glycerol and 2.00 M KOH at 180° C.). Key: ▲ Lactate; ✱ Formate; ▽Pyruvaldehyde; ⊙TSP (standard)

Given that maintaining high pH is necessary to minimize formic acid decomposition, further reactions were carried out to increase the effective base concentration by decreasing CO$_2$ pressure. A reaction with 26 bar CO$_2$ at 150° C. and 2 M KOH affords almost double the activity observed with 48 bar CO$_2$ (~600 turnovers in 24 hr, FIG. 5 and Table 1, Experiment 7). Thus, lower CO$_2$ pressure is favorable for both formic acid and lactic acid production. When the same reaction was performed at 180° C., the use of Catalyst 1a affords 1065 turnovers of formic acid and 1685 of lactic acid in 24 hr (FIG. 6), corresponding to 166 mM and 262 mM respectively. The reaction was monitored by $^1$H NMR (FIG. 7) until 86 hr, at which time TONs of lactic acid and formic acid reached 5046 and 2200 respectively.

Figures 8, 9:
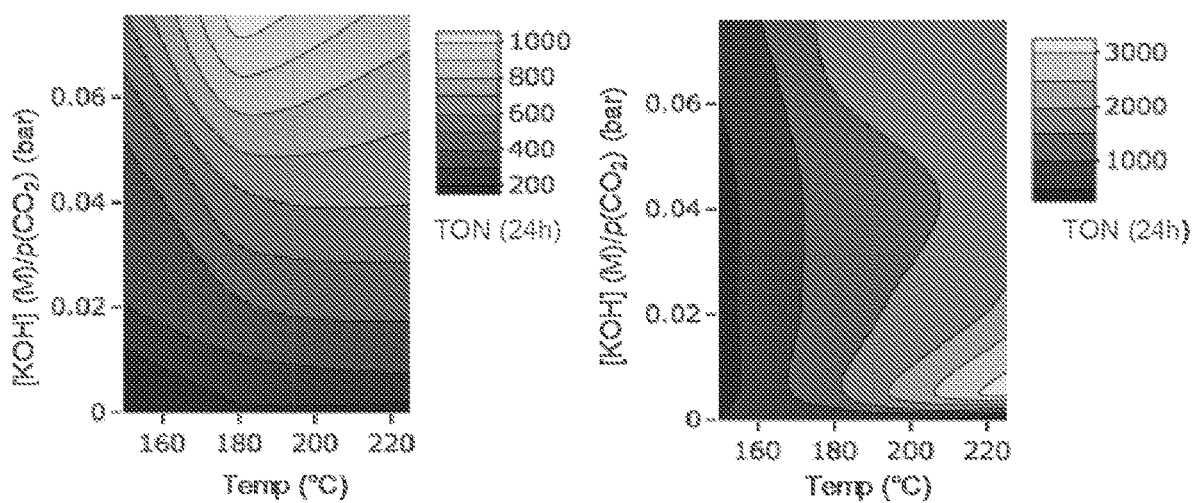

The effect of temperature, base concentration and CO$_2$ pressure are summarized by contour plots based on temperature and the "effective" base concentration (estimated as [KOH]/p(CO$_2$)) (FIGS. 8 and 9). Thus, optimal equimolar production of formic acid and lactic acid occurs when temperature and effective base concentration are maximized. However, higher lactic acid production can be achieved with higher reaction temperature and lower base concentration. The conditions can thus be used to "tune" the ratio of formic acid and lactic acid produced.

Figure 10:
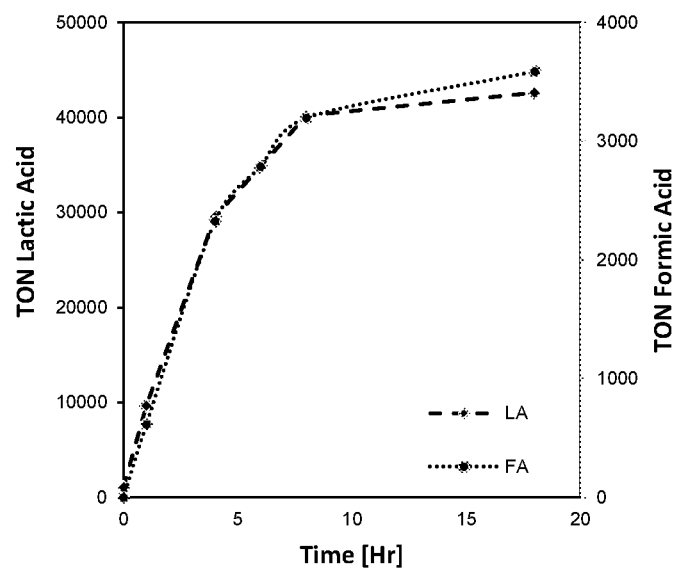
FIG. 10 is a graph showing the time course for production of formic acid, lactic acid and 1,2-PDO from the reaction of 2.00 M $K_2CO_3$ and glycerol using Catalyst 1a (1 mol %) at $N_2$ 26 bar, 6.85 M aqueous glycerol and 1.00 M KOH at 150° C.
Figure 11:
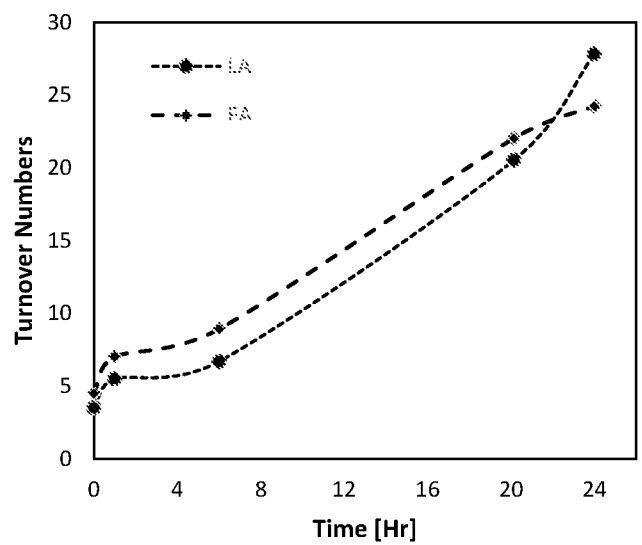
FIG. 11 is a graph showing the time course for production of formic acid and lactic acid from the reaction of $CO_2$ and glycerol using Catalyst 4a (1 mol %) at $pCO_2$ 46 bar, 6.85 M aqueous glycerol and 1.00 M KOH at 150° C.
Figure 12:
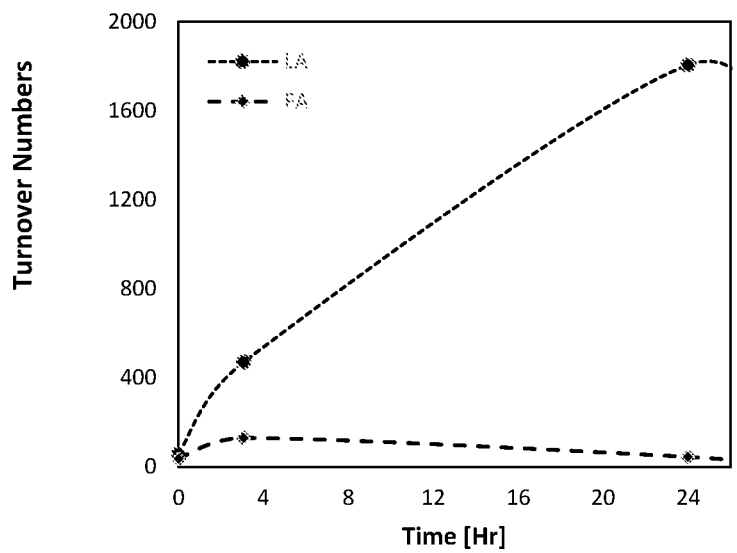
FIG. 12 is a graph showing the time course for production of formic acid and lactic acid from the reaction of $CO_2$ and glycerol using Catalyst 4a (1 mol %) at $pCO_2$ 46 bar, 6.85 M aqueous glycerol and 0.25 M KOH at 225° C.
Figure 13:
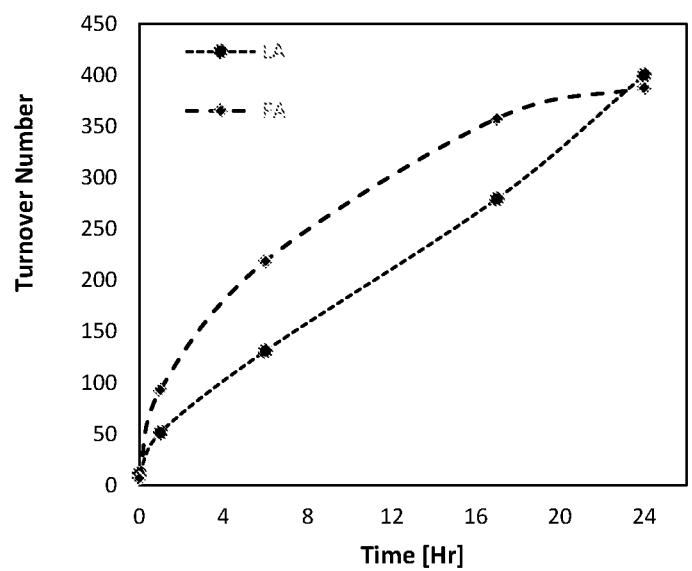
FIG. 13 is a graph showing the time course for production of formic acid and lactic acid from the reaction of $CO_2$ and glycerol using Catalyst 6b (1 mol %) at $pCO_2$ 46 bar, 6.85 M aqueous glycerol and 1.00 M KOH at 150° C.
Figure 14:
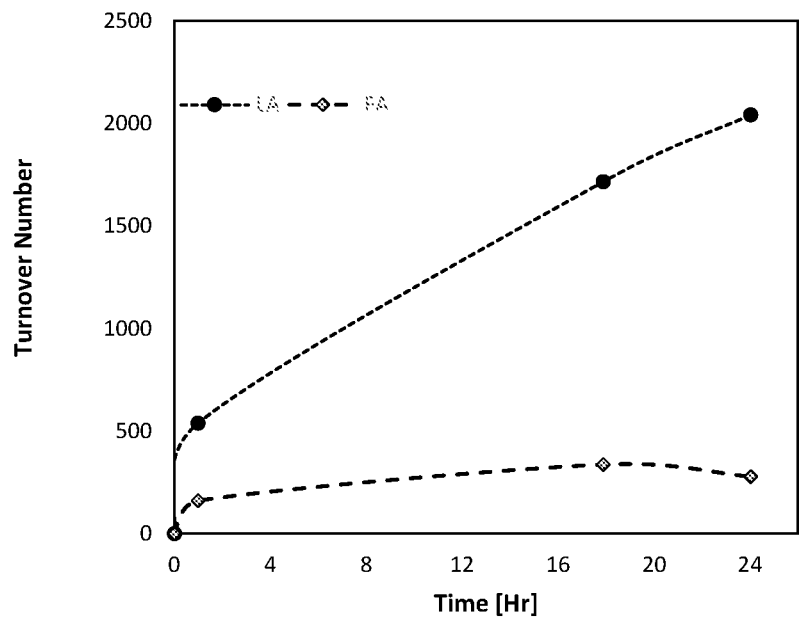
FIG. 14 is a graph showing the time course for production of formic acid and lactic acid from the reaction of $CO_2$ and glycerol using Catalyst 6b (1 mol %) at $pCO_2$ 46 bar, 6.85 M aqueous glycerol and 0.25 M KOH at 225° C.
Figure 15:
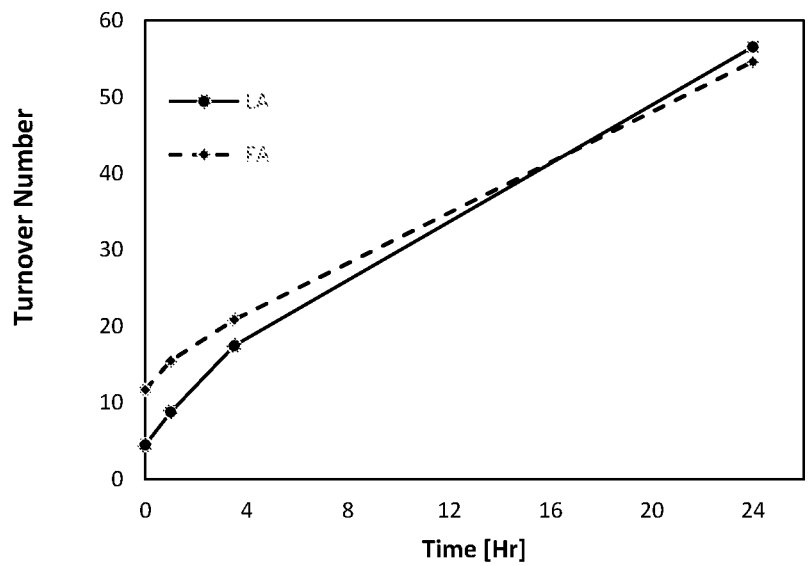
FIG. 15 is a graph showing the time course for production of formic acid and lactic acid from the reaction of $CO_2$ and glycerol using Catalyst 2a (1 mol %) at $pCO_2$ 46 bar, 6.85 M aqueous glycerol and 1.00 M KOH at 150° C.
Figure 16:
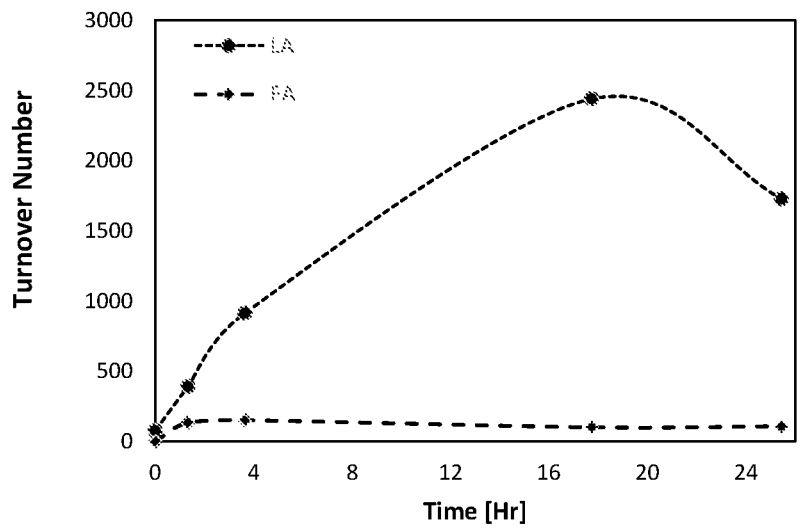
FIG. 16 is a graph showing the time course for production of formic acid and lactic acid from the reaction of $CO_2$ and glycerol using Catalyst 2a (1 mol %) at $pCO_2$ 46 bar, 6.85 M aqueous glycerol and 0.25 M KOH at 225° C.
Figure 17:
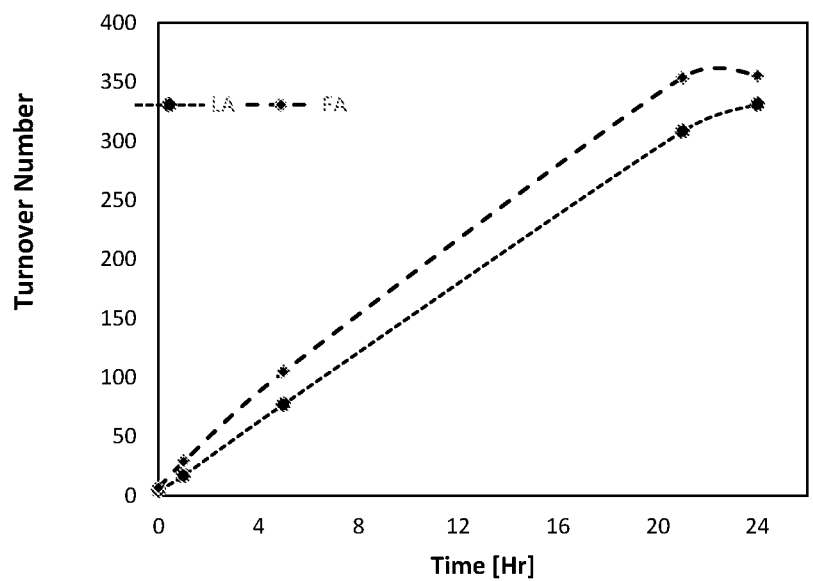
FIG. 17 is a graph showing the time course for production of formic acid and lactic acid from the reaction of $CO_2$ and glycerol using Catalyst 1a (1 mol %) at $pCO_2$ 46 bar, 6.85 M aqueous glycerol and 1.00 M KOH at 150° C.
Figure 18:
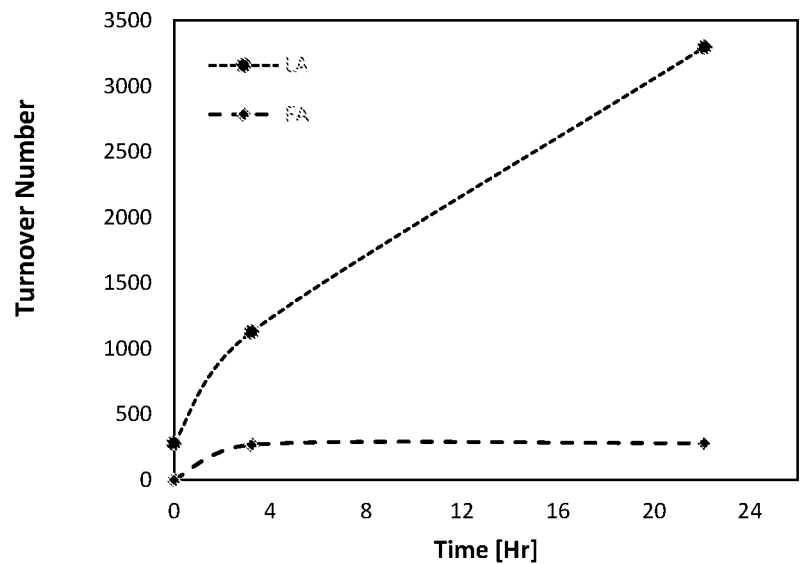
FIG. 18 is a graph showing the time course for production of formic acid and lactic acid from the reaction of $CO_2$ and glycerol using Catalyst 1a (1 mol %) at $pCO_2$ 46 bar, 6.85 M aqueous glycerol and 0.25 M KOH at 225° C.
Figure 19:
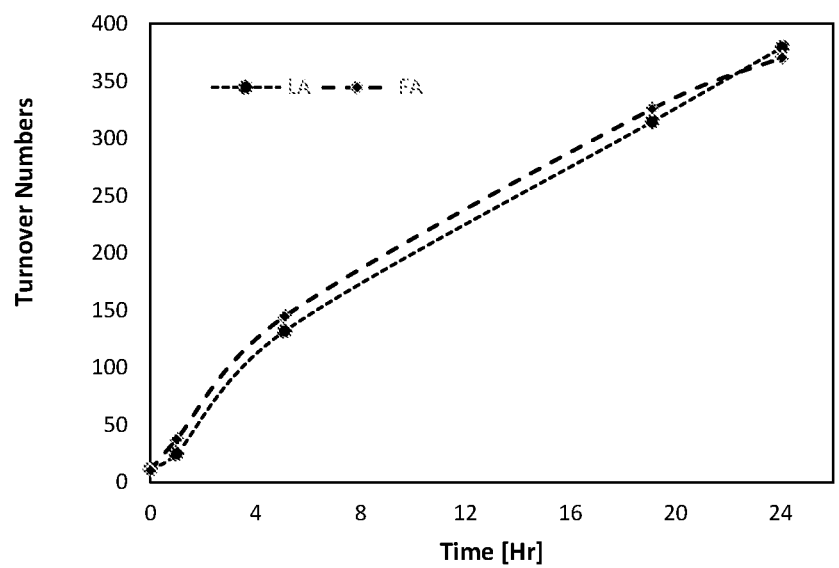
FIG. 19 is a graph showing the time course for production of formic acid and lactic acid from the reaction of $CO_2$ and glycerol using Catalyst 5a (1 mol %) at $pCO_2$ 46 bar, 6.85 M aqueous glycerol and 1.00 M KOH at 150° C.
Figure 20:
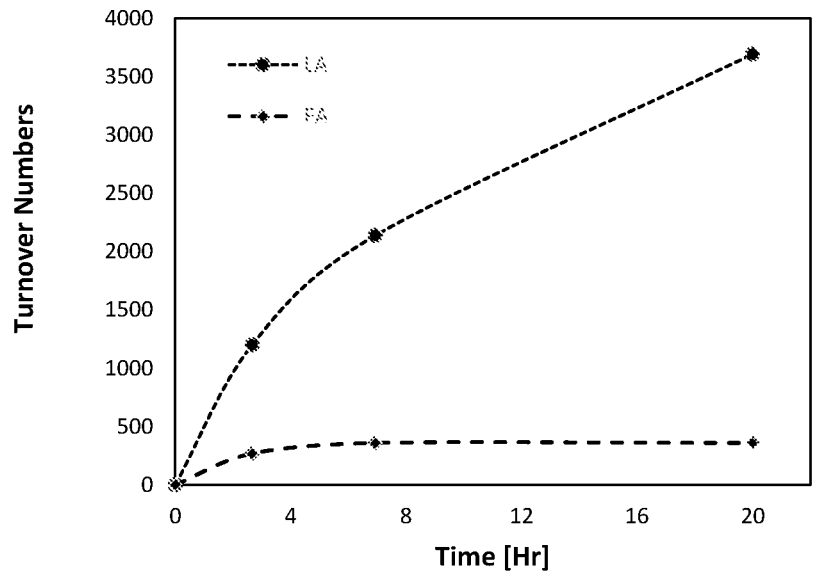
FIG. 20 is a graph showing the time course for production of formic acid and lactic acid from the reaction of $CO_2$ and glycerol using Catalyst 5a (1 mol %) at $pCO_2$ 46 bar, 6.85 M aqueous glycerol and 0.25 M KOH at 225° C.

Optimization Testing for Bicarbonate and Glycerol Transformation using Homogeneous Catalyst 1a. Given that $CO_2$ in the presence of KOH forms $K_2CO_3$, it is hypothesized that carbonate or hydrogen carbonate is being reduced. To test whether carbonate is a kinetically competent intermediate, a reaction with 2.0 M $K_2CO_3$ and 26 bar $N_2$ at 150° C. was conducted. Carbonate was selected over bicarbonate in order to increase initial pH. The initial pH of 12.1 dropped to 10.8 over 20 hours of reaction. The theoretical ratios of $HCO_3^-$:$CO_3^{2-}$ at pH 12.1 and 10.8 are 2:98 and 40:60 respectively, which is important because bicarbonate is likely the only species that can undergo transformation. In 20 hours, the reaction afforded 42610, 3588 and 5649 turnovers respectively of lactic acid, formic acid and 1,2-PDO (FIG. 10). The formic acid yield based on carbonate is 25% (505 mM). The higher lactic vs formic acid concentration observed is consistent with previous observations of dehydrogenation activity of Catalyst 1a at lower pH (See FIG. 4). 1,2-PDO is only observed under the lower pH conditions.

$CO_2$ and Glycerol Transformation using Various Homogeneous Catalysts. In view of the results of the Optimization testing using Catalyst 1a, the other homogeneous catalysts described herein were tested at two conditions: (i) 150° C., 1 M KOH and (ii) 225° C., 0.25M KOH. The pressure of $CO_2$ was maintained at 46 bar, and the most active catalyst was also screened also 150° C., 1 M KOH and 26 bar $CO_2$ pressure.

FIGS. 11-14 and 19-22 show the time courses for the Ir(III) and Ir(I) Catalysts 4a, 5a and 6b. First, it is noted that the trends observed for the 150° C. and 225° C. conditions are the same for the iridium catalysts as for the ruthenium catalyst 1a used in the reaction condition optimization. Namely, at the lower temperature conditions (150° C.) the FA and LA generation is equal, consistent with a transfer hydrogenation pathway, while at the higher temperature the LA generated far exceeds that of FA. Without being bound to any particular theory, it is believed this is likely due to concurrent transfer hydrogenation and acceptorless dehydrogenation of glycerol. Thus, one of skill can use the data of FIGS. 11-14 and 19-22 to estimate the propensity of each catalyst for both processes. Furthermore, it can be observed that at both temperatures the quantity of FA generated is comparable, so the transfer hydrogenation process is not highly sensitive to temperature. However, at 225° C. the quantity of FA generated levels off and actually decreases after a few hours of reaction. Without being bound to any particular theory, this is may be due to the decomposition of potassium formate, whose thermal stability is limited beyond 160° C., especially in the presence of a catalyst. Thus, despite the fact that similar FA concentrations (and TONs) are observed in the 150° C. and 225° C., at 225° C. the result of competing FA generation and decomposition is observed.

The activity of the three catalysts for the generation of FA at 150° C. shows that Catalysts 5a and 6b show comparable activity, reaching 370 and 356 turnovers respectively in 24 hours. Catalyst 4a, which only differs from Catalyst 5a by the presence of a Cp* ligand (substituting the acetate and iodide ligands of Catalyst 5a) is significantly less active than Catalysts 5a and 6b, reaching only 24 turnovers. Without being bound to any particular theory, it is believed this is a result of the strongly-binding Cp* ligand, which limits the number of open sites on the iridium.

At the higher temperature conditions (225° C.) catalyst 5a shows higher activity than catalysts 6b and 4a (3693, 2040 and 1804 turnovers in 24 hours, respectively, for lactic acid). Thus, it is likely that the hindrance that results from the Cp* ligand has a greater effect on the transfer hydrogenation activity as compared to the reduction in acceptorless dehydrogenation activity.

Comparing the activity of the two ruthenium(II) catalysts (i.e., Catalysts 1a and 2a) at both temperature conditions we observe that Catalyst 1a is significantly more active than Catalyst 2a for both processes (transfer hydrogenation and acceptorless dehydrogenation) (FIGS. 15-18). At 150° C. Catalyst 1a reaches 356 turnovers in 24 hours, vs 54 turnovers for Catalyst 2a. At the high temperature conditions Catalyst 1a reaches 3297 turnovers, vs 1728 for Catalyst 2a in 24 hours. Catalyst 2a also shows a decomposition of LA from 16 hours on, which could not be accounted for with another product, other than a solid precipitate, likely a polymer, which could not be identified. Without being bound to any particular theory, it is believed the higher activity of Catalyst 1a compared to Catalyst 2a is due to the in-situ formation of a CNC-Ru species, which has significantly higher activity for glycerol dehydrogenation than the bis-NHC Ru species in Catalyst 2a.

Figure 21:
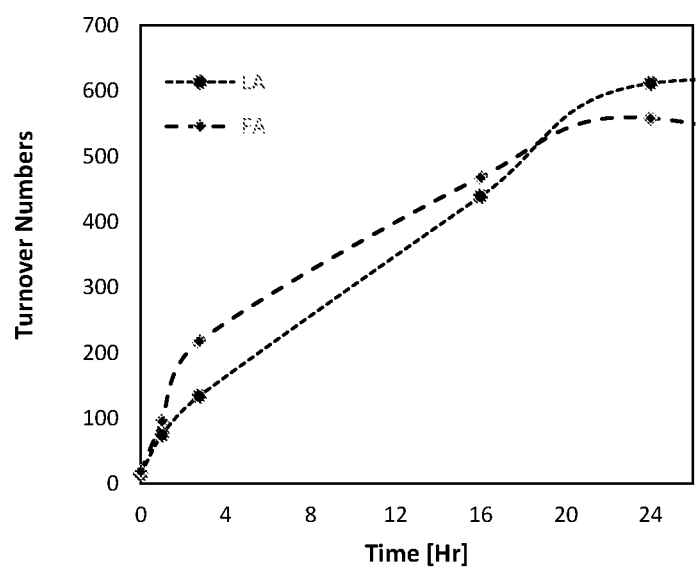
FIG. 21 is a graph showing the time course for production of formic acid and lactic acid from the reaction of $CO_2$ and glycerol using Catalyst 5a (1 mol %) at $pCO_2$ 26 bar, 6.85 M aqueous glycerol and 2.00 M KOH at 150° C.

The comparable activity under both conditions for Catalysts 5a, 1a and 6b indicates that under these conditions all catalysts are limited by presence of base and/or $CO_2$. To test whether the limitation of effective base concentration can distinguish the activity of the three, the activity of Catalyst 5a at the lower $CO_2$ pressure (26 bar) was tested, which resulted in a doubling of turnover numbers. As shown in FIG. 21, under the lower pressure conditions the activity of Catalyst 5a closely tracked that of Catalyst 1a, suggesting a base-limitation under these conditions.

Synthesis of Heterogeneous Catalysts

Single-site supported heterogeneous catalysts were formed by immobilizing a homogeneous catalyst as described above on a hydrotalcite material (HT). HTs are basic clays consisting of cationic sheets that are held together by interlayer anions and water molecules, forming a layered double hydroxide (LDH) structure. Naturally-occurring HTs consist of $Mg^{2+}$ and $Al^{3+}$ in the cationic sheets, but synthetic HTs can be prepared with other compatible transition metal ions such as, for example Zn, Fe, Cr, Ni, and Cu ions (with regard to Cu ions, hereinafter referred to as a "CuHT"), substituted in the cationic layer. The synthetic HTs share similar morphology but have tunable electronic properties, allowing optimization of activity and stability of the immobilized catalyst using the support properties. The immobilized catalysts were synthesized in two steps: first, synthesis of a homogeneous catalyst as described above, and second, simultaneous in situ HT synthesis and homogeneous catalyst immobilization thereon via a continuous flow process using two separate feeds consisting of 1) a solution containing metal precursors for the formation of an HT (for example Mg, Al, and optionally Cu salts) and 2) an alkaline solution with the homogeneous catalyst that are mixed at a connection point and ageing. In some instances, the solid support, HT or otherwise can be prefabricated. In such instances, immobilization of the homogeneous catalyst can be accomplished via a continuous flow process using two separate feeds consisting of 1) a solution containing the prefabricated solid support and 2) an alkaline solution with the homogeneous catalyst that are mixed at a connection point and ageing.

In a first example, heterogeneous Catalyst 1a-HT was prepared via an 'in-situ' synthesis method, where the palladium complex was immobilized during the formation of HT. A 60-mL syringe was charged with 50 mL of solution A, containing $Mg(NO_3)_2$ (2.376 g, 9.27 mmol) and $Al(NO_3)_3$ (1.225 g, 3.27 mmol). A second 60 mL syringe was charged with 50 mL of solution B, containing NaOH (1.012, 25.3 mmol), $Na_2CO_3$ (0.112 g, 1.0 mmol), and catalyst 1a (0.1 mmol). The two syringes were connected via tubing with a 'Y' connecter and mixed via syringe pump at a rate of 4 mL/min, dropping into a beaker with 100 mL of DI water with stirring set to 600 RPM. After the addition was complete, stirring continued and the solution was aged at 60° C. for 2 hours. After cooling to room temperature, the solid was filtered and washed with DI water until the filtrate was no longer basic to litmus paper. The collected solid was ground into a powder and dried under vacuum at 60° C. overnight.

In a second example, heterogeneous Catalyst 2a-HT was prepared via an 'in-situ' synthesis method, where the palladium complex was immobilized during the formation of HT. A 60-mL syringe was charged with 50 mL of solution A, containing $Mg(NO_3)_2$ (2.376 g, 9.27 mmol) and $Al(NO_3)_3$ (1.225 g, 3.27 mmol). A second 60 mL syringe was charged with 50 mL of solution B, containing NaOH (1.012, 25.3 mmol), $Na_2CO_3$ (0.112 g, 1.0 mmol), and catalyst 2a (0.1 mmol). The two syringes were connected via tubing with a 'Y' connecter and mixed via syringe pump at a rate of 4 mL/min, dropping into a beaker with 100 mL of DI water with stirring set to 600 RPM. After the addition was complete, stirring continued and the solution was aged at 60° C. for 2 hours. After cooling to room temperature, the solid was filtered and washed with DI water until the filtrate was no longer basic to litmus paper. The collected solid was ground into a powder and dried under vacuum at 60° C. overnight.

In a third example, heterogeneous Catalyst 3a-HT was prepared via an 'in-situ' synthesis method, where the palladium complex was immobilized during the formation of HT. A 60-mL syringe was charged with 50 mL of solution A, containing $Mg(NO_3)_2$ (2.376 g, 9.27 mmol) and $Al(NO_3)_3$ (1.225 g, 3.27 mmol). A second 60 mL syringe was charged with 50 mL of solution B, containing NaOH (1.012, 25.3 mmol), $Na_2CO_3$ (0.112 g, 1.0 mmol), and catalyst 3a (0.1 mmol). The two syringes were connected via tubing with a 'Y' connecter and mixed via syringe pump at a rate of 4 mL/min, dropping into a beaker with 100 mL of DI water with stirring set to 600 RPM. After the addition was complete, stirring continued and the solution was aged at 60° C. for 2 hours. After cooling to room temperature, the solid was filtered and washed with DI water until the filtrate was no longer basic to litmus paper. The collected solid was ground into a powder and dried under vacuum at 60° C. overnight.

In a fourth example, heterogeneous Catalyst 4a-HT was prepared via an 'in-situ' synthesis method, where the palladium complex was immobilized during the formation of HT. A 60-mL syringe was charged with 50 mL of solution A, containing $Mg(NO_3)_2$ (2.376 g, 9.27 mmol) and $Al(NO_3)_3$ (1.225 g, 3.27 mmol). A second 60 mL syringe was charged with 50 mL of solution B, containing NaOH (1.012, 25.3 mmol), $Na_2CO_3$ (0.112 g, 1.0 mmol), and catalyst 4a (0.1 mmol). The two syringes were connected via tubing with a 'Y' connecter and mixed via syringe pump at a rate of 4 mL/min, dropping into a beaker with 100 mL of DI water with stirring set to 600 RPM. After the addition was complete, stirring continued and the solution was aged at 60° C. for 2 hours. After cooling to room temperature, the solid was filtered and washed with DI water until the filtrate was no longer basic to litmus paper. The collected solid was ground into a powder and dried under vacuum at 60° C. overnight.

In a fifth example, heterogeneous Catalyst 5a-CuHT was prepared via an 'in-situ' synthesis method, where the palladium complex was immobilized during the formation of HT. A 60-mL syringe was charged with 50 mL of solution A, containing $Mg(NO_3)_2$ (2.376 g, 9.27 mmol), $Cu(NO_3)_2$ (0.464 g, 2.47 mmol) and $Al(NO_3)_3$ (1.225 g, 3.27 mmol). A second 60 mL syringe was charged with 50 mL of solution B, containing NaOH (1.012, 25.3 mmol), $Na_2CO_3$ (0.112 g, 1.0 mmol), and catalyst 5a (0.1 mmol). The two syringes were connected via tubing with a 'Y' connecter and mixed via syringe pump at a rate of 4 mL/min, dropping into a beaker with 100 mL of DI water with stirring set to 600 RPM. After the addition was complete, stirring continued and the solution was aged at 60° C. for 2 hours. After cooling to room temperature, the solid was filtered and washed with DI water until the filtrate was no longer basic to litmus paper. The collected solid was ground into a powder and dried under vacuum at 60° C. overnight.

In a sixth example, heterogeneous Catalyst 6a-HT was prepared via an 'in-situ' synthesis method, where the palladium complex was immobilized during the formation of HT. A 60-mL syringe was charged with 50 mL of solution A, containing $Mg(NO_3)_2$ (2.376 g, 9.27 mmol) and $Al(NO_3)_3$ (1.225 g, 3.27 mmol). A second 60 mL syringe was charged with 50 mL of solution B, containing NaOH (1.012, 25.3 mmol), $Na_2CO_3$ (0.112 g, 1.0 mmol), and catalyst 6a (0.1 mmol). The two syringes were connected via tubing with a 'Y' connecter and mixed via syringe pump at a rate of 4 mL/min, dropping into a beaker with 100 mL of DI water with stirring set to 600 RPM. After the addition was complete, stirring continued and the solution was aged at 60° C. for 2 hours. After cooling to room temperature, the solid was filtered and washed with DI water until the filtrate was no longer basic to litmus paper. The collected solid was ground into a powder and dried under vacuum at 60° C. overnight.

Figure 22:
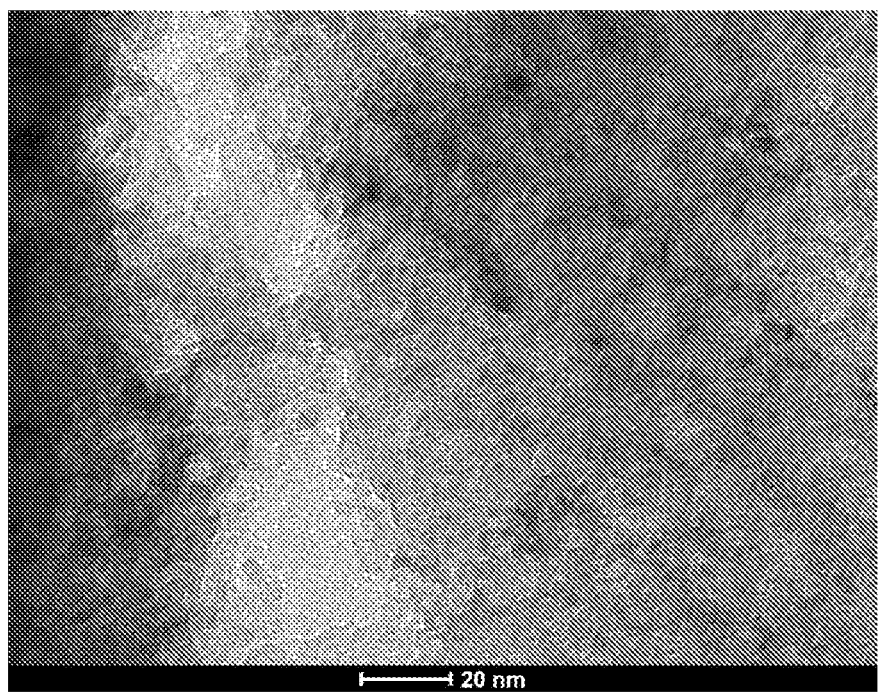
FIG. 22 is a transmission electron microscopy (TEM) image of a heterogeneous catalyst, Catalyst 5a-CuHT, formed in accordance with various aspects of the present disclosure.
Figure 23:
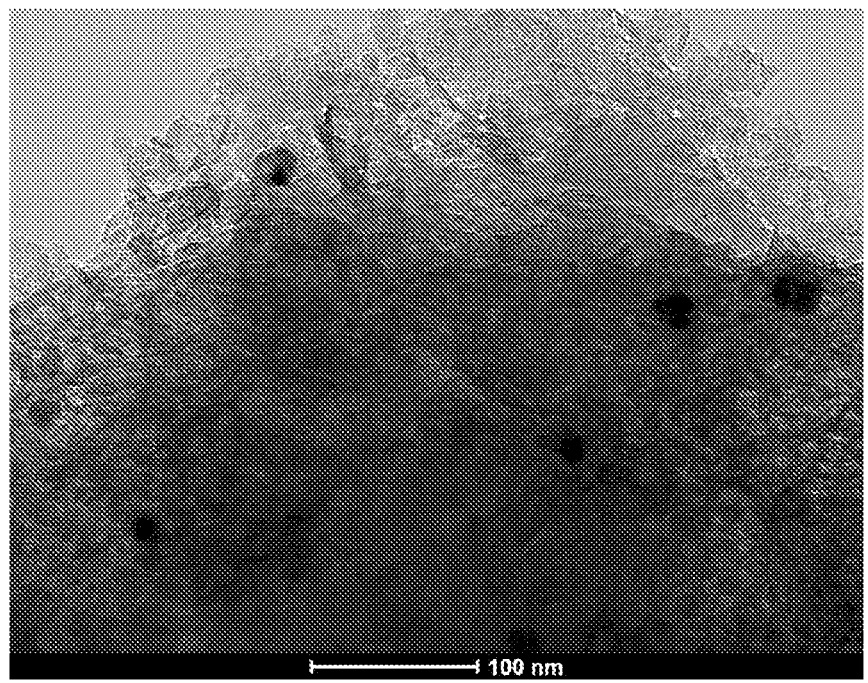
FIG. 23 is a TEM image of another heterogeneous catalyst, Catalyst 2a-HT, formed in accordance with various aspects of the present disclosure.
Figure 24:
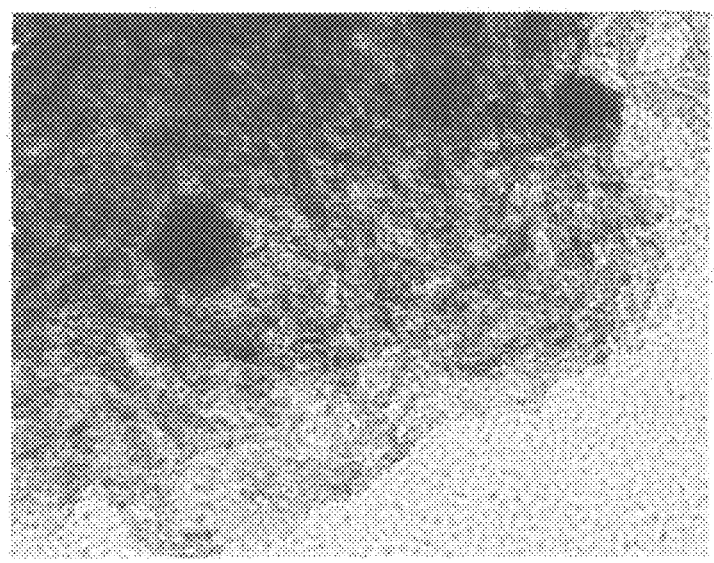
FIG. 24 is another TEM image of Catalyst 2a-HT.
Figure 25:
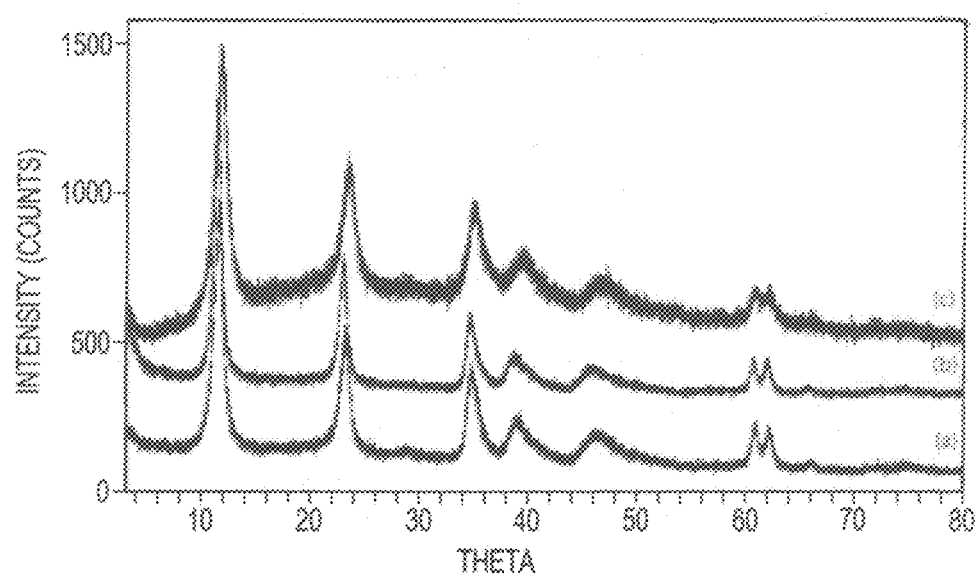
FIG. 25 is a graph showing powder x-ray diffraction (PXRD) profiles for (a) Catalyst 5a-CuHT, (b) Catalyst 2a-HT, and (c) Catalyst 2a-CuHT, respectively.

FIG. 22 is a transmission electron microscopy (TEM) image of Catalyst 5a-CuHT. FIGS. 23-24 are TEM images of Catalyst 2a-HT. As can be observed in the TEM images of each heterogeneous catalyst, uniform clusters of distributed throughout their respective HT structures. Without being bound to any particular theory, it is believed that the observed clusters correspond to regions rich with Catalysts 5a and 2a. FIG. 25 is a graph showing powder x-ray diffraction (PXRD) profiles for (a) Catalyst 5a-CuHT, (b) Catalyst 2a-HT, and (c) Catalyst 2a-CuHT, respectively. The PXRD images indicate no major changes as a result catalyst immobilization on HTs. The lack of change in the interlayer spacing of the layered HTs suggests that the catalytic complexes are immobilized on the surface of the HT. Energy dispersive x-ray (EDX) mapping studies performed on each of Catalysts 2a-HT and 5a-CuHT also indicate successful immobilization of homogeneous Catalysts 5a and 2a into the HT structure. Inductively Coupled Plasma-Atomic Emission Spectroscopy (ICP-AES) indicated that ~1 mol % of the metal composition of the HTs were composed of an immobilized homogeneous catalyst.

Figure 26:
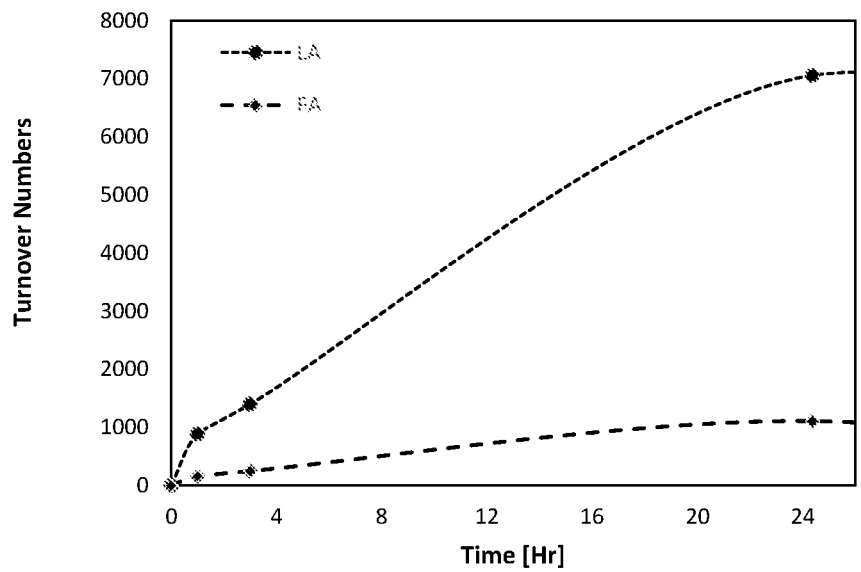
FIG. 26 is a graph showing the time course for production of formic acid and lactic acid under batch conditions from the reaction of $CO_2$ and glycerol using Catalyst 1a-HT at $pCO_2$ 26 bar and 225° C.

$CO_2$ and Glycerol Transformation Under Batch Conditions Using Heterogeneous Catalyst 1a-HT In one experiment, glycerol and $CO_2$ transformation at 225° C. and 45 bar ($pCO_2$) was performed as previously described using 5-7 mg of Catalyst 1a-HT and IM KOH. As shown in FIG. 26, TONs of 741 and 4,423 were achieved after 24 hours for FA and LA, respectively, and 833 and 4,987 after 40 hours for FA and LA, respectively.

Figure 27:
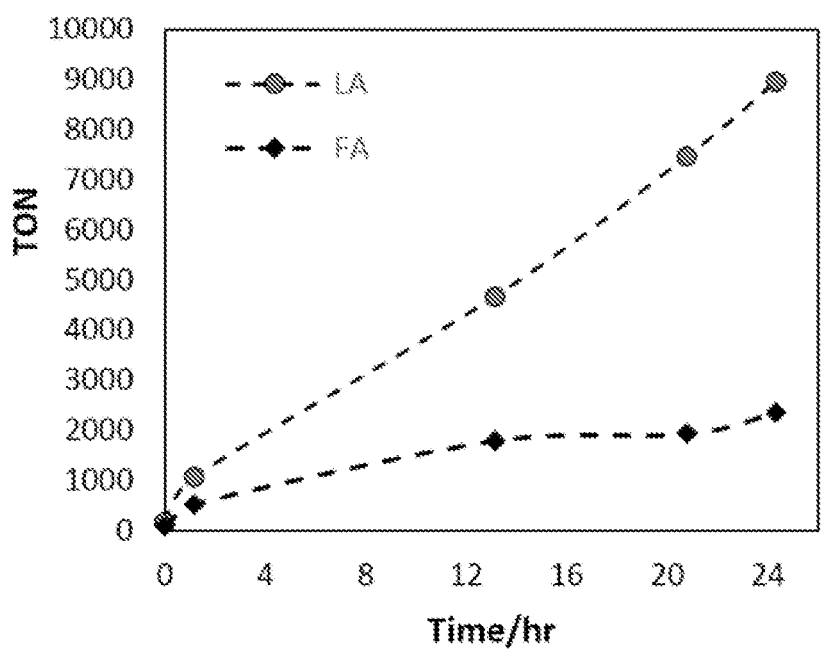
FIG. 27 is a graph showing the time course for production of formic acid and lactic acid under batch conditions from the reaction of $CO_2$ and glycerol using Catalyst 2a-HT at $pCO_2$ 45 bar and 225° C.

In another experiment, glycerol and $CO_2$ transformation at 225° C. and 45 bar ($pCO_2$) were performed as previously described using 5-7 mg of Catalyst 2a-HT and 1M KOH. FIG. 27 is a graph showing the TONs achieved between 0-24 hours for FA and LA in this experiment.

Figure 28:
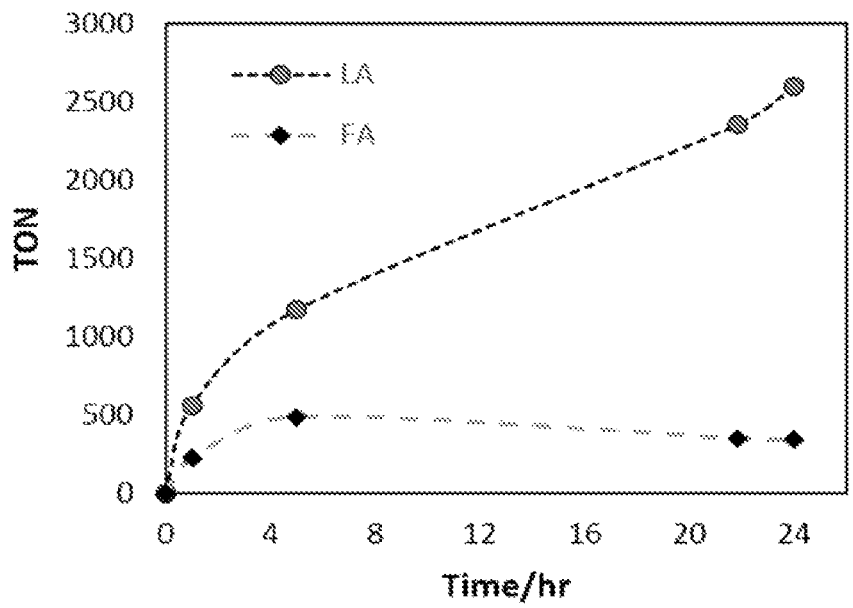
FIG. 28 is a graph showing the time course for production of formic acid and lactic acid under batch conditions from the reaction of $CO_2$ and glycerol using Catalyst 6a-HT at $pCO_2$ 45 bar and 225° C.

In yet another experiment, glycerol and $CO_2$ transformation at 225° C. and 45 bar ($pCO_2$) were performed as previously described using 5-7 mg of Catalyst 6a-HT and 1M KOH. FIG. 28 is a graph showing the TONs achieved between 0-24 hours for FA and LA in this experiment.

Figure 29:
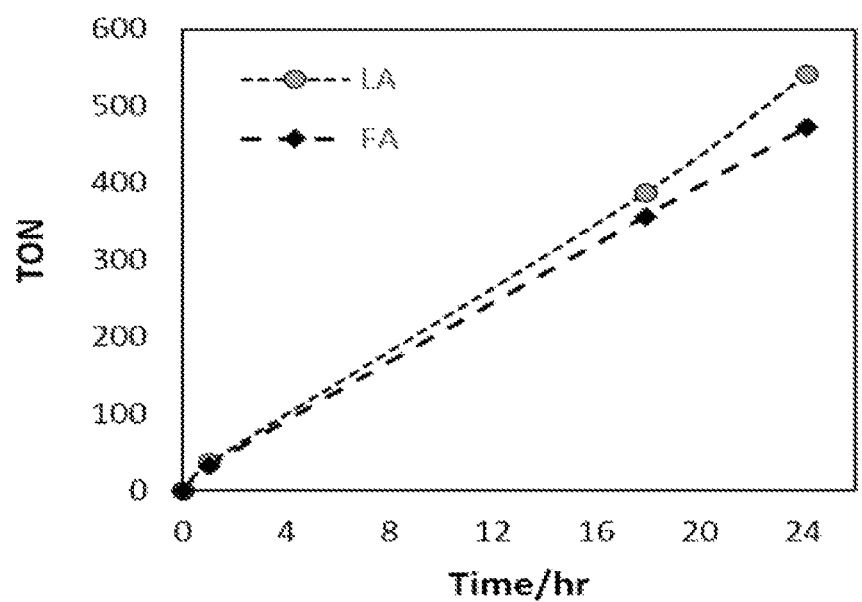
FIG. 29 is a graph showing the time course for production of formic acid and lactic acid under batch conditions from the reaction of $CO_2$ and glycerol using Catalyst 6a-HT at $pCO_2$ 46 bar and 150° C.

In yet another experiment, glycerol and $CO_2$ transformation at 150° C. and 46 bar ($pCO_2$) were performed as previously described using 5-7 mg of Catalyst 6a-HT and 1M KOH. FIG. 29 is a graph showing the TONs achieved between 0-24 hours for FA and LA in this experiment.

Figure 30:
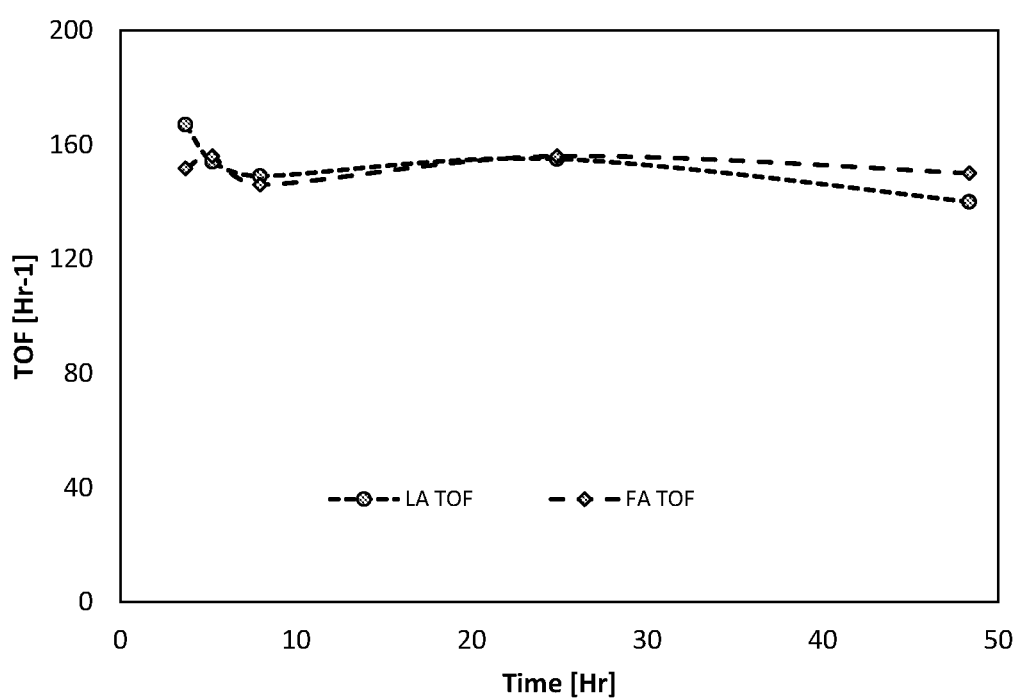
FIG. 30 is a graph showing the time course for production of formic acid and lactic acid under continuous flow conditions from the reaction of $CO_2$ and glycerol using Catalyst 1a-HT at $pCO_2$ 45 bar, 225° C. and a $CO_2$ flow rate of 32 ml/min.

$CO_2$ and Glycerol Transformation under Continuous Flow Conditions using Heterogeneous Catalyst 1a-HT. At 225° C. and 45 bar (650 psi) and using a $CO_2$ flow rate of 32 ml/min, the highest catalytic activity in Parr experiments for Catalyst 1a-HT (5-7 mg) achieved 140-160 turnovers per hour for LA and FA (FIG. 30). Flow experiments showed little to no loss in activity after the first 3 hours with experiments lasting over 300 hrs.

Although the present invention and its objects, features and advantages have been described in detail, other embodiments are encompassed by the invention. All references cited herein are incorporated by reference in their entireties. Finally, those skilled in the art should appreciate that they can readily use the disclosed conception and specific embodiments as a basis for designing or modifying other structures for carrying out the same purposes of the present invention without departing from the scope of the invention as defined by the appended claims.

What is claimed is:

1. A catalyst for the transformation of glycerol and any one $CO_2$, a carbonate salt and a bicarbonate salt, the catalyst comprising a catalytically active compound, or salt thereof, of formula (I):

where
M is Fe, Ru, Os, Co, Rh, and Ir;
NHC is an N-heterocyclic carbene ligand;
R is an alkylene or an arylene group;
linker is sulfonate;
L is a neutral ligand;
X is an anionic ligand;
a is an integer ranging from 1 to 3;
b is an integer ranging from 0 to 3; and
c is an integer ranging from 0 to 3, and
wherein,
when M is Fe, Os, Co, Rh or Ir, NHC is selected from the group consisting of 2-(imidazol-1-yl)pyridine, 1-methylimidazole, 2-(1H-imidazol-1-ylmethyl)pyridine, 1,3-di(1H-imidazol-1-yl)benzene, 1,6-di(1H-imidazol-1-yl)benzene, 1,2-bis(imidazol-1'-yl)ethane, N-trimethylsilylimidazole, 1-(2-chlorophenyl)imidazole, 1-(3-bromobenzyl)-1H-imidazole, 1-(3-chlorophenyl)imidazole, 1-(3-fluorophenyl)imidazole, 1-(4-chlorophenyl)imidazole, 1-(4-fluorophenyl)imidazole, 1-(m-tolyl)imidazole, 1-(3-aminopropyl)imidazole, 1-(diethoxymethyl)imidazole, 1H-imidazole-1-carboxylic acid-3-butenyl ester, 3-buten-2-yl 1H-imidazole-1-carboxylate, propargyl 1H-imidazole-1-carboxylate, 1-(p-toluenesulfonyl)imidazole, 1-(2-naphthoyl)imidazole, 1-(trifluoroacetyl)imidazole, 1-(tert-butyldimethylsilyl)imidazole, 1-(methyldithiocarbonyl)imidazole, 1-(trifluoromethanesulfonyl)imidazole, 1-(dimethylsulfamoyl)imidazole, ethyl 1H-imidazole-1-carboxylate, methyl 1H-imidazole-1-carboxylate, 1-(4-methoxyphenyl)-1H-imidazole, 1-(11-mercaptoundecyl)imidazole, 1-[2-(trifluoromethyl)phenyl]imidazole, 1-[2-(3-bromophenoxy)ethyl]-1H-imidazole, and 1-(3-hydroxypropyl)-1H-imidazole, and
when M is Ru, NHC is selected from the group consisting of 2-(imidazol-1-yl)pyridine, 2-(1H-imidazol-1-ylmethyl)pyridine, 1,3-di(1H-imidazol-1-yl)benzene, 1,6-di(1H-imidazol-1-yl)benzene, and 1,2-bis(imidazol-1'-yl)ethane.

2. The catalyst of claim 1, further comprising a solid support, wherein the catalytically active compound is immobilized to the solid support.

3. The catalyst of claim 2, wherein the catalytically active compound is immobilized to the solid support via
ionic or Coulombic interactions; or
a covalent bond; or
an indirect bond via a secondary linking compound, the secondary linking compound covalently bonded with both of the linker and the solid support.

4. The catalyst of claim 2, wherein the solid support has any one of a 3D structure, a 2D structure, a 1D structure, and a 0D structure.

5. The catalyst of claim 2, wherein the solid support is porous or non-porous.

6. The catalyst of claim 2, wherein the solid support is a hydrotalcite material.

7. The catalyst of claim 1, wherein the M of the catalytically active compound is any one of Rh, Fe, Co, Ru and Ir.

8. The catalyst of claim 1, wherein
the R of the catalytically active compound is any one of propylene, butylene, 1,8-naphthylene, phenylene, and benzylene; or
the neutral ligand L of the catalytically active compound is any one of carbon monoxide (CO), p-cymene, 1,5-cyclooctadiene (COD), 1,3-cyclohexadiene, 1,4-cyclohexadiene, ethylene, pyridine, a thiol, an alcohol, a phosphine, a trialkyl phosphine, a triaryl phosphine or phosphine oxide; or
the anionic ligand X of the catalytically active compound is any one of pentamethylcyclopentadienyl (Cp*), nitrosyl (NO), nitrile (CN), acetate, allyl, a halide, carbonate, triflate and trifluoroacetate.

9. The catalyst of claim 1, wherein the catalytically active compound is

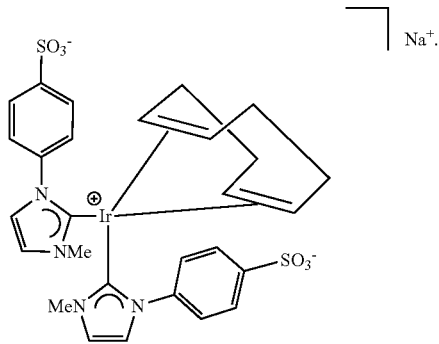

10. The catalyst of claim 1, wherein the catalytically active compound is

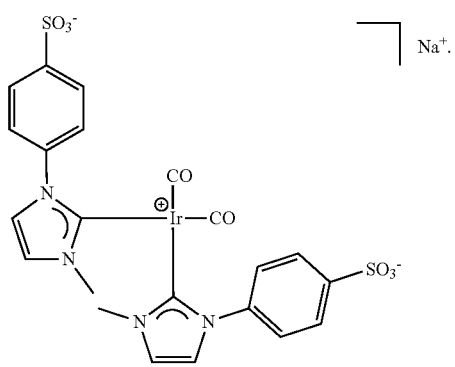

11. The catalyst of claim 1, wherein the catalytically active compound is

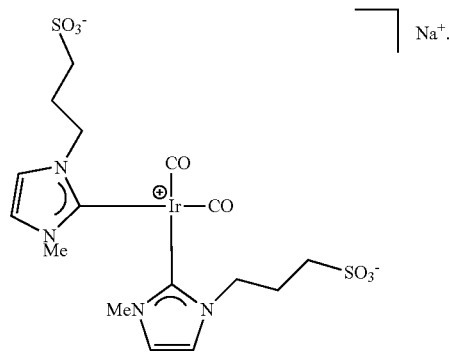

12. A method of making formic acid and lactic acid, the method comprising reacting, in a reaction solution, a carbon feedstock and glycerol in the presence of a catalyst, wherein the catalyst comprises a catalytically active compound according to claim 1.

13. The method of claim 12, wherein
the carbon feedstock is $CO_2$, a carbonate salt, or a bicarbonate salt; and/or
the reaction solution further comprises at least one of water and a base.

14. The method of claim 12, wherein the method is performed under batch conditions or continuous flow conditions.

15. The method of claim 14, wherein the method is performed in an autoclave, the autoclave comprising:
a glass insert;
a means for agitating a reaction solution within the autoclave; and
a means for removing a sample of the reaction solution from the autoclave.

16. The method of claim 14, wherein
when the method is performed under batch conditions, the method is performed in a microwave reactor, and
when the method is performed under continuous flow conditions, the method is performed in a continuous flow reactor.

17. The method of claim 12, wherein
the method is performed at a temperature ranging from about 25° C. to about 400° C.; or
the method takes place in the presence of one or more gas(es) and a pressure ranging from about 1 bar to about 100 bar, the one or more gas(es) comprising $CO_2$, argon and nitrogen.

18. The method of claim 12, wherein the method is performed using the catalytically active compound in an amount ranging from about 0.25 mol % to about 4 mol % relative to glycerol.

19. The method of claim 12, wherein the reaction solution has a glycerol concentration ranging from about 1 M to about 15 M.

20. The method of claim 12, wherein the method takes place in the presence of a flow of $CO_2$, at a flow rate ranging from about 10 ml/min to about 50 ml/min.

* * * * *